(12) United States Patent
Chen et al.

(10) Patent No.: US 12,156,910 B2
(45) Date of Patent: Dec. 3, 2024

(54) LIVE ATTENUATED INFLUENZA B VIRUS COMPOSITIONS METHODS OF MAKING AND USING THEREOF

(71) Applicant: Versitech Limited, Hong Kong (CN)

(72) Inventors: Honglin Chen, Hong Kong (CN); Pui Wang, Hong Kong (CN); Kwok Yung Yuen, Hong Kong (CN)

(73) Assignee: VERSITECH LIMITED, Hong Kong (CN)

( * ) Notice: Subject to any disclaimer, the term of this patent is extended or adjusted under 35 U.S.C. 154(b) by 475 days.

(21) Appl. No.: 17/294,603

(22) PCT Filed: Nov. 16, 2018

(86) PCT No.: PCT/CN2018/115938
§ 371 (c)(1),
(2) Date: May 17, 2021

(87) PCT Pub. No.: WO2020/097923
PCT Pub. Date: May 22, 2020

(65) Prior Publication Data
US 2022/0016232 A1    Jan. 20, 2022

(51) Int. Cl.
*A61K 39/145*    (2006.01)
*A61P 31/16*    (2006.01)
*A61K 39/00*    (2006.01)

(52) U.S. Cl.
CPC ............ *A61K 39/145* (2013.01); *A61P 31/16* (2018.01); *A61K 2039/5254* (2013.01)

(58) Field of Classification Search
None
See application file for complete search history.

(56) References Cited

U.S. PATENT DOCUMENTS

| | | | |
|---|---|---|---|
| 5,057,540 | A | 10/1991 | Kensil |
| 6,090,406 | A | 7/2000 | Popescu |
| 6,207,646 | B1 | 3/2001 | Krieg |
| 6,239,116 | B1 | 5/2001 | Krieg |
| 6,299,884 | B1 | 10/2001 | Van Nest |
| 6,348,450 | B1 | 2/2002 | Tang |
| 6,451,325 | B1 | 9/2002 | Van Nest |
| 8,592,196 | B2 | 11/2013 | Kittel |
| 2009/0232843 | A1 | 9/2009 | Niman |
| 2017/0202955 | A1 | 7/2017 | Podda |

FOREIGN PATENT DOCUMENTS

| | | |
|---|---|---|
| CN | 101796190 | 8/2010 |
| CN | 105518129 | 4/2016 |
| CN | 107208071 | 9/2017 |
| CN | 110732021 | 1/2020 |
| EP | 0109942 | 5/1984 |
| EP | 0689454 | 1/1996 |
| EP | 0835318 | 4/1998 |
| WO | 1990014837 | 12/1990 |
| WO | 1994000153 | 1/1994 |
| WO | 1995017211 | 6/1995 |
| WO | 1996011711 | 4/1996 |
| WO | 1996033739 | 10/1996 |
| WO | 1998042375 | 10/1998 |
| WO | 1998057659 | 12/1998 |
| WO | 1999011241 | 3/1999 |
| WO | 1999027960 | 6/1999 |
| WO | 1999027961 | 6/1999 |
| WO | 1999052549 | 10/1999 |
| WO | 2000007621 | 2/2000 |
| WO | 2001021152 | 3/2001 |
| WO | 2001021207 | 3/2001 |
| WO | 2001095935 | 12/2001 |
| WO | 2002026757 | 4/2002 |
| WO | 2002074244 | 9/2002 |
| WO | 2003028760 | 4/2003 |
| WO | 2003035836 | 5/2003 |
| WO | 2009080806 A2 | 7/2009 |
| WO | 2009080806 A3 | 10/2009 |

(Continued)

OTHER PUBLICATIONS

Andrianov, et al., "Preparation of hydrogel microspheres by coacervation of aqueous polyphosphazene solutions", Biomaterials, 19(1-3): 109-115 (1998).
Barr, et al., "ISCOMs and other saponin based adjuvants", Advanced Drug Delivery Reviews, 32(3): 247-27 (1998).
Beignon, et al., "The LTR72 mutant of heat-labile enterotoxin of *Escherichia coli* enhances the ability of peptide antigens to elicit CD4(+) T cells and secrete gamma interferon after coapplication onto bare skin", Infection and Immunity, 70(6):3012-3019 (2002).
Bhagat, et al., "CpG penta- and hexadeoxyribonucleotides as potent immunomodulatory agents", BBRC, 300(4): 853-861 (2003).
Blackwell, et al., "CpG-A-induced monocyte IFN-gamma-inducible protein-10 production is regulated by plasmacytoid dendritic cell-derived IFN-alpha", J. Immunol., 170(8): 4061-4068 (2003).
Caini, et al., "Distribution of influenza virus types by age using case-based global surveillance data from twenty-nine countries, 1999-2014", BMC Infect. Dis., 18(1):269, 10 pages (2018).

(Continued)

*Primary Examiner* — Benjamin P Blumel
(74) *Attorney, Agent, or Firm* — PABST PATENT GROUP LLP

(57) ABSTRACT

The NS1 protein of influenza virus is a key virulent element with multi-functional roles in virus replication and acts as a strong interferon (IFN) antagonist. A live attenuated virus (LAIV) is provided using a master backbone, which contains the influenza B (HK8038) virus and includes a deletion of the NS1 coding region (DelNS1). The LAIV is based on novel adaptive mutations, which support DelNS1 influenza B live attenuated virus (LAIV) replication in vaccine producing cells. DelNS1 influenza B LAIV shows spontaneous cold adaption with preference to grow at 30-33° C. but restriction at 37-39° C. The LAIV can be used to protect a subject, against a lethal challenge of antigenic distant influenza B viruses. DelNS1 LAIV with adaptive mutations for growing in vaccine producing systems is an important strategy for making highly attenuated and immunogenic live attenuated influenza vaccines with the ability to induce broad cross protective immunity for seasonal influenza.

14 Claims, 6 Drawing Sheets
Specification includes a Sequence Listing.

(56) References Cited

FOREIGN PATENT DOCUMENTS

| WO | 2012062218 | 5/2012 |
|---|---|---|
| WO | 2019241758 | 12/2019 |

OTHER PUBLICATIONS

Dauber, et al., "The Influenza B Virus Nonstructural NS1 Protein Is Essential for Efficient Viral Growth and Antagonizes Beta Interferon Induction", J. Virol., 78(4):1865-1872 (2004).

Glezen, et al., "The burden of influenza B: a structured literature review", Am. J. Public Health, 103(3):e43-51 (2013).

Hai, et al., "A reassortment-Incompetent Live Attenuated Ingluenza Virus Vaccine for Protection against Pandemic Virus Strains", J. of Virology, 85(14):6832-6843 (2011).

Hai, et al., "Influenza B virus NS1-truncated mutants: live-attenuated vaccine approach", J. Virology, 82(21):10580-10590 (2008).

Hoffmann, et al., "A DNA transfection system for generation of influenza A virus from eight plasmids", PNAS, 97(11):6108-13 (2000).

International Search Report for PCT/CN2018/115938 dated Aug. 8, 2019.

International Search Report for PCT/CN2021/072657 dated Apr. 22, 2021.

International Search Report for PCT/CN2021/075527 dated May 10, 2021.

Iuliano, et al., "Estimates of global seasonal influenza-associated respiratory mortality: a modelling study", Lancet, 391(10127):1285-1300 (2018).

Jin, et al., "Live attenuated influenza vaccine", Curr. Top. Microbial. Immunol., 386:181-204 (2015).

Johnson, et al, "Synthesis and biological evaluation of a new class of vaccine adjuvants: aminoalkyl glucosaminide 4-phosphates (AGPs)", Bioorg. Med. Chem. Lett., 9(15):2273-2278 (1999).

Jones, "Resiquimod 3M", Curr. Opin. Investig. Drugs, 4(2):214-218 (2003). Abstract Only.

Kandimalla, et al., "Divergent synthetic nucleotide motif recognition pattern: design and development of potent immunomodulatory oligodeoxyribonucleotide agents with distinct cytokine induction profiles", Nucleic Acids Research, 31(9):2393-2400 (2003a).

Kandimalla, et al., "Toll-like receptor 9: modulation of recognition and cytokine induction by novel synthetic CpG DNAs", Biochemical Society Transactions, 31 (part 3): 654-658 (2003b).

Krieg, "CpG motifs: the active ingredient in bacterial extracts?", Nature Medicine, 9(7): 831-835 (2003).

Krieg, "From A to Z on CpG", Trends in Immunology, 23(2): 64-65 (2002).

McCluskie, et al., "Parenteral and mucosal prime-boost immunization strategies in mice with hepatitis B surface antigen and CpG DNA ", FEMS Immunology and Medical Microbiology, 32(3): 179-185 (2002).

Meraldi, et al., "OM-174, a new adjuvant with a potential for human use, induces a protective response when administered with the synthetic C-terminal fragment 242-310 from the circumsporozoite protein of Plasmodium berghei", Vaccine, 21(19-20): 2485-2491 (2003).

Pajak, et al., "The adjuvant OM-174 induces both the migration and maturation of murine dendritic cells in vivo", Vaccine, 21(9-10): 836-84 (2003).

Partidos, et al., "Heat-labile enterotoxin of *Escherichia coli* and its site-directed mutant LTK63 enhance the proliferative and cytotoxic T-cell responses to intranasally co-immunized synthetic peptides", Immunol. Lett., 67(3):209-216 (1999).

Peppoloni, et al., "Mutants of the *Escherichia coli* heat-labile enterotoxin as safe and strong adjuvants for intranasal delivery of vaccines", Vaccines, 2(2):285-293 (2003).

Pica, et al., "NS1-Truncated Live Attenuated Virus Vaccine Provides Robust Protection to Aged Mice from Viral Challenge", J. Virology, 86(19):10293-10301 (2012).

Pine, et al., "Intranasal immunization with influenza vaccine and a detoxified mutant of heat labile enterotoxin from *Escherichia coli* (LTK63)", J. Control. Release, 85(1-3):263-270 (2002).

Pizza, et al., "LTK63 and LTR72, two mucosal adjuvants ready for clinical trials", Int. J. Med. Microbiol., 290(4-5): 455-461 (2003).

Pizza, et al., "Mucosal vaccines: non toxic derivatives of LT and CT as mucosal adjuvants", Vaccine, 19(17-19): 2534-2541 (2001).

Podda, "The adjuvanted influenza vaccines with novel adjuvants: experience with the MF59-adjuvanted vaccine", Vaccine, 19(17-19):2673-2680 (2001).

Ryan, et al., "Mutants of *Escherichia coli* heat-labile toxin act as effective mucosal adjuvants for nasal delivery of an acellular pertussis vaccine: differential effects of the nontoxic AB complex and enzyme activity on Th1 and Th2 cells", Infection and Immunity, 67(12):6270-6280 (1999).

Scharton-Kersten, et al., "Transcutaneous Immunization with Bacterial ADP-Ribosylating Exotoxins, Subunits, and Unrelated Adjuvants", Infection and Immunity, 68(9): 5306-5313 (2000).

Singh, et al., "A novel bioadhesive intranasal delivery system for inactivated influenza vaccines", J. Cont. Rel., 70(3):267-276 (2001).

Sjolander, et al., "Uptake and adjuvant activity of orally delivered saponin and ISCOM™ vaccines", Advanced Drug Delivery Reviews, 32(2-3): 321-338 (1998).

Stanley, "Imiquimod and the imidazoquinolones: mechanism of action and therapeutic potential", Clin. Exp. Dermatol., 27(7): 571-577 (2002).

Talon, et al., "Influenza A and B viruses expressing altered NS1 proteins: A vaccine approach", PNAS, 97(8):4309-1314 (2000).

Thompson, et al., "Influenza-associated hospitalizations in the United States", JAMA, 292(11):1333-1340 (2004).

Wang, et al. "Generation of DeINS 1 Influenza Viruses: a Strategy for Optimizing Live Attenuated Influenza Vaccines", mBio, 10(5): e02180-19 (2019).

Wressnigg, et al., "Development of a live-attenuated influenza deltaNS1 intranasal vaccine candidate", Vaccine, 27: 2851-2857 (2009).

Zhang, et al., "Influenza Research Database: An integrated bioinformatics resource for influenza virus research", Nucleic Acids Research, 45(D1): D466-D474 (2017).

Zheng, et al, "An A14U Substitution in the 3= Noncoding Region of the M Segment of Viral RNA Supports Replication of Influenza Virus with an NS1 Deletion by Modulating Alternative Splicing of M Segment mRNAs", J. Virology, 89(20):10273-10285 (2015).

Zhu, et al. "Effect of human activated NRAS on replication of deINS 1 H5NI influenza virus in MDCK cells", Virology Journal, 8:240, 5 pages (2011).

FIG. 1A

| Segment | Mutations |
|---|---|
| PA | T210C |
| NA | T1424C |
| NP | C182T |
| M | A281G |

FIG. 1B

SEQUENCE LISTING

```
<160> NUMBER OF SEQ ID NOS: 26

<210> SEQ ID NO 1
<211> LENGTH: 2426
<212> TYPE: DNA
<213> ORGANISM: Artificial Sequence
<220> FEATURE:
<223> OTHER INFORMATION: synthetic sequence

<400> SEQUENCE: 1
agtactggtc gacctccgaa gttggggggg agcagaagcg gagcgttttc aagatgacat      60
```

```
tggccaaaat tgaattgtta aaacaactgc taagggacaa tgaagccaaa acagttttga      120
agcaaacaac agtagaccaa tataacataa taagaaaatt caatacatca aggattgaaa      180
agaatccttc actaaggatg aagtgggcca tgtgttctaa ttttcccttg gctctaacca      240
agggcgatat ggcaaacaga atccccttgg aatacaaagg gatacaactc aaaacaaatg      300
ctgaagacat aggaaccaaa ggccaaatgt gctcaatagc agcagttact tggtggaata      360
catatggacc aataggagat actgaaggtt cgaagggt ctacgaaagc ttttttctca        420
gaaaaatgag acttgacaac gccacttggg gccgaataac ttttggccca gttgaaagag      480
tgagaaaaag ggtactgcta aaccctctca ccaaggaaat gcctccggat gaggcgagca      540
atgtgataat ggaaatattg ttccctaaag aagcaggaat accaagagaa tccacttgga      600
tacataggga actgataaaa gaaaaagag aaaaattgaa aggaacaatg ataactccaa       660
tcgtactggc atacatgctt gaaagagaac tggttgctcg aagaagattc ttgccagtgg      720
caggagcaac atcagctgag ttcatagaaa tgctacactg cttacaaggt gaaaattgga      780
gacaaatata tcacccagga gggaataaat taactgagtc caggtctcaa tcaatgatag      840
tagcttgtag aaaaataatc agaagatcaa tagtcgcttc aaacccactg gagctagctg      900
tagaaattgc aaacaagact gtgatagata ctgaaccttt aaagtcatgt ctggcagcca      960
tagacggagg tgatgtagct tgtgacataa taagagctgc attaggacta aagatcagac     1020
aaagacaaag atttggacgg cttgagctaa aagaatatc aggaagagga ttcaaaaatg      1080
atgaagaaat attaataggg aacggaacaa tacagaagat tggaatatgg gacggggaag     1140
aggagttcca tgtaagatgt ggtgaatgca ggggaatact aaaaaagagt aaaatgaaac     1200
tggaaaaact actgataaat tcagccaaaa aggaggatat gagagattta ataatcttat     1260
gcatggtatt ttctcaagac actaggatgt tccaaggggt gagaggagaa ataaatttc      1320 ttaatcgagc aggccaactt ttatctccaa tgtaccaact ccaacgatat ttttttgaata     1380 gaagcaacga ccttttttgat caatgggggt atgaggaatc acccaaagca agtgaactac     1440
atgggataaa tgaatcaatg aatgcatctg actatacatt gaaagggatt gtagtgacaa     1500
gaaatgtaat tgacgacttt agctctactg aaacagaaaa agtatccata acaaaaaatc     1560
ttagtttaat aaaaaggact ggggaagtca taatgggagc taatgacgtg agtgaattag     1620
aatcacaagc acagctgatg ataacatatg atacacctaa aatgtgggaa atgggaacaa     1680
ccaaagaact ggtgcaaaac acttatcaat gggtgctaaa aaacttggtg acactgaagg     1740 ctcagttttct tctaggaaaa gaggacatgt tccaatggga tgcatttgaa gcatttgaga     1800
gcataattcc tcagaagatg gctggtcaat acagtggatt tgcaagagca gtgctcaaac     1860
aaatgagaga ccaggaggtt atgaaaactg accagttcat aaagttgttg ccttttttgtt     1920 tctcaccacc aaaattaagg agcaatgggg agccttatca attcttaaaa cttgtgttga     1980
aaggaggagg ggaaaatttc atcgaagtaa ggaaagggtc ccctctattt tcctataatc     2040
cacaaacaga agtcctaact atatgcggca gaatgatgtc attaaagggg aaaattgaag     2100
atgaagaaag gaatagatca atggggaatg cagtattagc aggctttctc gttagtggca     2160
aatatgaccc agatcttgga gatttcaaaa ctattgaaga acttgaaaag ctgaaaccag     2220
gggaaaaggc aaacatctta ctttatcaag gaaaccagt taaagtagtt aaaaggaaaa      2280
ggtatagtgc tttgtccaat gacatttcac aaggaattaa gagacaaaga atgacagttg     2340
agtccatggg gtgggccttg agctaatata aattttatcca ttaattcaat gaacgcaatt     2400
gagtgaaaaa tgctcgtgtt tctact                                          2426
```

<210> SEQ ID NO 2
<211> LENGTH: 2369
<212> TYPE: DNA
<213> ORGANISM: Artificial Sequence
<220> FEATURE:
<223> OTHER INFORMATION: synthetic sequence

<400> SEQUENCE: 2

| | | | | | |
|---|---|---|---|---|---|
| agcagaagcg | gagcctttaa | gatgaatata | aatccttatt | ttctcttcat | agatgtgccc | 60 |
| gtacaggcag | caatttcaac | aacattccca | tacactggtg | ttccccctta | ttctcatgga | 120 |
| acaggaacag | gctacacaat | agacaccgtg | atcagaacgc | atgagtactc | aaacaagggg | 180 |
| aaacagtaca | tttctgatgt | tacaggatgc | acaatggtag | atccaacaaa | tggaccatta | 240 |
| cccgaagata | atgagccgag | tgcctatgcg | caattagatt | gcgttttaga | ggctttggat | 300 |
| agaatggatg | aagaacaccc | aggtctttt | caagcagcct | cacagaatgc | tatggaggcc | 360 |
| ctaatggtca | caactgtaga | caaattaacc | caggggagac | agactttga | ttggacagta | 420 |
| tgcagaaacc | aacctgctgc | aacggcactg | aacacaacaa | taacctcttt | taggttgaat | 480 |
| gatttaaatg | gagccgacaa | aggtggatta | atacctttt | gtcaggatat | cattgattca | 540 |
| ttagaccgac | ctgaaatgac | tttcttctca | gtaaagaata | taagaaaaa | attgcctgcc | 600 |
| aaaaacagaa | agggtttcct | cataaagagg | ataccaatga | aggtaaaaga | caaataacc | 660 |
| aaagtggaat | acatcaaaag | agcattatca | ttaaacacaa | tgacaaaaga | cgctgaaaga | 720 |
| ggcaaattga | aaagaagagc | gattgccact | gctggaatac | aaatcagagg | gtttgtatta | 780 |
| gtagttgaaa | acttggctaa | aaatatatgt | gaaaatctag | aacaagtgg | tttaccagta | 840 |
| ggtgaaacg | agaagaaagc | caaactgtca | aacgcagtgg | ccaaaatgct | cagtaactgc | 900 |
| ccaccaggag | ggattagcat | gacagtaaca | ggagacaata | caaaatggaa | tgaatgttta | 960 |
| aacccaagaa | tcttttggc | tatgactgaa | agaataacca | gagacagccc | aatttggttc | 1020 |
| agggatttt | gtagtatagc | accggtcctg | ttctccaata | agatagcaag | attggggaaa | 1080 |
| gggtttatga | taacaagcaa | aacaaaaga | ctgaaggctc | aaataccttg | tcctgatctg | 1140 |
| tttagtatac | cattagaaag | atataatgaa | gaaacaaggg | caaaattgaa | aaagctaaaa | 1200 |
| ccattcttca | atgaagaagg | aactgcatct | ttgtcgcctg | gatgatgat | gggaatgttt | 1260 |
| aatatgctat | ctaccgtgtt | gggagtagct | gcactaggta | tcaagaacat | tggaaacaaa | 1320 |
| gaatacttat | gggatggact | gcaatcttct | gatgattttg | ctctatttgt | taatgcaaag | 1380 |
| gatgaagaaa | catgtatgga | aggaataaac | gactttacc | gaacatgtaa | attattggga | 1440 |
| ataaacatga | gcaaaagaa | aagttactgt | aatgagactg | gaatgtttga | atttacaagc | 1500 |
| atgttctaca | gatggatt | tgtatctaat | tttgcaatgg | aactcccttc | gtttgggtt | 1560 |
| gctggagtaa | atgaatcagc | agatatggca | ataggaatga | caataaa | gaacaacatg | 1620 |
| atcaacaatg | ggatgggtcc | agcaacagca | caaacagcca | tacagttatt | catagctgat | 1680 |
| tatagataca | cctacaaatg | ccacaggga | gattccaaag | tagaaggaaa | gagaatgaaa | 1740 |
| atcataaagg | agttatggga | aaacactaaa | ggaagagatg | gtctattagt | agcagatggt | 1800 |
| gggcccaaca | tttacaattt | gagaaacttg | catatcccag | aaatagtatt | aaagtataat | 1860 |
| ctaatggacc | ctgaatacaa | agggcggtta | cttcatcctc | aaaatccctt | tgtgggacat | 1920 |
| ttgtctattg | aaggcatcaa | agaggcagat | ataccccag | cacatggtcc | agtaaagaaa | 1980 |
| atggactacg | atgcggtgtc | tggaactcat | agttggagaa | ccaaaagaaa | cagatctata | 2040 |

```
ctaaacactg atcagaggaa catgattctt gaggaacaat gctacgctaa atgttgcaac    2100
ctatttgagg cctgttttaa cagtgcatca tacaggaagc cagtgggtca acatagcatg    2160
cttgaggcta tggcccacag attaagaatg gatgcacgat tagattatga atcagggaga    2220
atgtcaaagg atgattttga gaaagcaatg gctcaccttg gtgagattgg gtacatataa    2280
gcttcgaaga tgtttatggg gttattggtc accattgaat acatgcgata cacaaatgat    2340
taaaatgaaa aaaggctcgt gtttctact                                      2369
```

<210> SEQ ID NO 3  
<211> LENGTH: 2305  
<212> TYPE: DNA  
<213> ORGANISM: Artificial Sequence  
<220> FEATURE:  
<223> OTHER INFORMATION: synthetic sequence

<400> SEQUENCE: 3

```
agcagaagcg gtgcgtttga tttgtcataa tggatacttt tattacaaga aacttccaga     60
ctacaataat acaaaaggcc aaaaacacaa tggcagaatt tagtgaagat cctgaattgc    120
aaccagcaat gctattcaat atctgcgtcc atctagaggt ttgctatgta ataagtgaca    180
tgaattttct tgacgaagaa ggaaaagcac atatagcatt agaaggacaa gggaaagaac    240
aaaacttgag accacaatat gaagtaattg agggaatgcc aagaaccata gcatggatgg    300
tccagagatc cttagctcaa gagcatggaa tagagactcc caagtatctg gctgatttgt    360
ttgattataa aaccaaaaga tttatagaag ttggaataac aaaaggattg gctgatgatt    420
acttttggaa aaagaaagaa aagttgggaa atagcatgga actgatgata ttcagctaca    480
atcaagacta ctcgttaagt aatgaatcct cattggatga ggaagggaaa gggagagtgc    540
taagcagact cacagaactt caggctgagt taagtctgaa aaacttatgg caagttctca    600
taggagagga agatgttgaa aagggaattg attttaaact tggacaaaca atatctagac    660
taagggatat atctgttccg gctggttttt ccaattttga aggaatgagg agctacatag    720
acaatataga cccaaaagga gcaatagaga gaatctagc aaggatgtct cccttagtat    780
cagtcacacc taaaaagtta acatggggag acctaagacc gataggggcct cacatttatg    840 accatgagct accagaagtt ccatataatg cctttcttct aatgtctgat gaactgggac    900
tggccaatat gactgaggga aaatccaaaa accgaagac attagccaaa gaatgtctag    960
aaaagtactc aacactacgg gatcaaactg acccaatatt aataatgaaa agcgaaaaag    1020
ctaacgaaaa tttcctatgg aagctttgga gagactgtgt aaacacaata agtaatgagg    1080
aaacaagtaa cgagttacag aaaccaatt atgccaaatg gctacagggg gacggattaa    1140
cataccagaa aataatgaaa gaagtagcaa tagatgacga acaatgtgc caagaagagc    1200 ctaaatcccc taacaaatgt agagtggctg cttgggttca aacagagatg aatctattga    1260
gcactctgac aagtaaaaga gctctggacc taccagaaat agggcccagac atagcacccg    1320 tggagcatgt aggaagtgaa agaaggaaat actttgttaa tgaaatcaac tactgtaagg    1380
cctctacagt tatgatgaag tatgtgcttt tcacacttc attgttgaat gaaagcaatg    1440
ccagcatggg aaaatacaaa gtaataccaa taaccaatag agtagtaaat gaaaaggag    1500 aaagtttcga catgcttac ggtctagcgg ttaaaggaca atctcatctg aggggagata    1560
ctgatgttgt aacagttgta actttcgaat ttagtggtac agatccaaga gtggactcag    1620
gaaagtggcc aaaatatact gtgtttagga ttggctccct atttgtgagt gggagggaa    1680 aatctgtgta cttgtattgc cgagtgaatg gcacaaataa gatccaaatg aaatggggaa    1740
```

```
tggaagctag aagatgtttg cttcaatcaa tgcaacaaat ggaggcaatt gttgaacagg    1800
aatcatcaat acaaggatat gacatgacca aagcctgttt caagggagac agagtaaata    1860
gccccaaaac tttcagtatt ggaactcaag aaggaaaact agtaaaagga tcctttggaa    1920
aaacactaag agtaatattt actaaatgct tgatgcacta tgtatttgga aatgcccaat    1980
tggaggggtt tagtgccgag tctaggagac ttctactgtt gattcaagca ttaaaggaca    2040
gaaagggccc ctgggtgttc gacttagagg gaatgtattc tggaatagaa gaatgtatta    2100
gcaacaaccc ttgggtaata cagagtgtat actggttcaa tgaatggttg gctttgaaa     2160 aggaggggag taaagtgttg gaatcagtgg atgaaataat ggatgaataa aaggaaatgg    2220
tactcaattt ggtactattt tgttcattat gtatctaaac atccaataaa aagaaccaag    2280
aatcaaaaat gcacgtgttt ctact                                          2305

<210> SEQ ID NO 4
<211> LENGTH: 1882
<212> TYPE: DNA
<213> ORGANISM: Artificial Sequence
<220> FEATURE:
<223> OTHER INFORMATION: synthetic sequence

<400> SEQUENCE: 4
agcagaagca gagcattttc taatatccac aaaatgaagg caataattgt actactcatg      60
gtagtaacat ccaatgcaga tcgaatctgc actgggataa catcgtcaaa ctcaccacat     120
gtcgtcaaaa ctgctactca agggaggtc aatgtgactg gtgtaatacc actgacaaca      180
acacccacca atctcatttt gcaaatctc aaaggaacag aaaccagagg gaaactatgc      240
ccaaaatgcc ccaactgcac agatctggac gtagccttgg gcagaccaaa atgcacggga    300
aaaatacccc tcggcaagagt ttcaatactc catgaagtca gacctgttac atctgggtgc    360
tttcctataa tgcacgacag aacaaaaatt agacagctgc ctaaccttct ccgaggatac    420
gaacatatca gattatcaac tcataacgtt atcaatgcag aaagtgcacc aggaggaccc    480
tacaaaattg gaacctcagg gtcttgcccc aacgttacca atggaaacgg atttttcgca    540
acaatggctt gggccgtccc aaaaaacgac aaaaacaaaa cagcaacaga tccattaaca    600
atagaagtac catacatttg tacagaagga gaagaccaaa ttaccgtttg ggggttccac    660
tctgataacg agatccaaat ggcaaagctc tatgggggact caaagcccca gaagttcacc    720
tcatctgcca acggagtgac cacacattac gtttcacaga ttggtggctt cccaaatcaa    780
acagaagacg gaggactacc acaaagtggt agaattgttg ttgattacat ggtacaaaaa    840
tctgggaaaa caggaacaat taccctatcaa agaggtattt tattgcctca aaaggtgtgg    900
tgcgcaagtg gcaggagcaa ggtaataaaa ggatccttgc ctttaattgg agaagcagat    960
tgcctccacg aaaaatacgg tggattaaac aaaagcaagc cttactacac agggaacat    1020 gcaaaggcca taggaaattg cccaatatgg gtgaagacac ccttgaagct ggccaatgga    1080
accaaatata gacctcctgc aaaactatta aaggaaggg gtttcttcgg agctattgct    1140
ggtttcttag aaggaggatg ggaaggaatg attgcaggtt ggcacggata cacgtcccat    1200
ggggcacatg gagtagcggt ggcagcagac cttaagagca ctcaagaggc cataaacaag    1260
ataacaaaaa atctaaactc tttgagtgag ctggaagtaa agaatcttca aagactaagc    1320
ggtgccatgg atgaactcca caacgaaata ctagaactag acgagaaagt agatgatctc    1380
agagctgata caataagctc acaaatagaa ctcgcagtcc tgctttccaa tgaaggaata    1440
```

| ataaacagtg aagatgaaca tctcttggcg cttgaaagaa agctgaagaa aatgctgggg | 1500 |
| ccctctgctg tagagatagg gaatggatgc tttgaaacca acacaagtg caaccagacc | 1560 |
| tgtctcgaca gaatagctgc tggtaccttt gacgcaggag aattttctct ccccaccttt | 1620 |
| gattcactga atattactgc tgcatcttta aatgacgatg gattggataa tcataccata | 1680 |
| ctgctttact actcaactgc tgcctccagt ttggctgtaa cactgatgat agctatcttt | 1740 |
| gttgtttata tggtctccag agacaatgtt tcttgctcca tctgtctata agggaagtta | 1800 |
| agccctgtgt tttcctttgt tgtagtgctt gtttgcttgt tgccattaca agaaacgtt | 1860 |
| attgaaaaat gctcttgtta ct | 1882 |

<210> SEQ ID NO 5
<211> LENGTH: 1844
<212> TYPE: DNA
<213> ORGANISM: Artificial Sequence
<220> FEATURE:
<223> OTHER INFORMATION: synthetic sequence

<400> SEQUENCE: 5

| agcagaagca cagcattttc ttgtgaactt caagcaccag taaagaact gaaaatcaaa | 60 |
| atgtccaaca tggatattga cggtataaac actgggacag ttgacaaaac accggaagaa | 120 |
| ataacttctg gaaccagtgg gacaaccaga ccaatcatta gaccagcaac ccttgcccca | 180 |
| ctaagcaaca aacgaacccg taacccatcc ccggaaagag caactacaag cagtgaagat | 240 |
| gatgtcggaa ggaaaaccca aaagaaacag accccgacag agataaagaa gagcgtctac | 300 |
| aacatggtgg tgaaactggg cgaattctat aaccagatga tggtcaaagc tggactcaat | 360 |
| gatgacatgg agagaaacct aatccaaaat gcgcatgccg tggaaagaat tctattggct | 420 |
| gccactgatg acaagaaaac cgatttccag aagaaaaaga atgccagaga tgtcaaagaa | 480 |
| gggaagaag aaatagatca aacaaaaca ggaggcacct tttataagat ggtaagagat | 540 |
| gataaaacca tctactttag ccctataaga attaccttt taaaagaaga ggtgaaaaca | 600 |
| atgtacaaaa ccaccatggg gagtgatggc ttcagtggac taaatcacat aatgattggg | 660 |
| cattcacaga tgaatgatgt ctgtttccaa agatcaaagg cactaaaag agttggactt | 720 |
| gatccttcat taatcagtac ctttgcggga agcacagtcc ccagaagatc aggtgcgact | 780 |
| ggtgttgcaa tcaaaggagg tggaactta gtggctgaag ccattcgatt tataggaaga | 840 |
| gcaatggcag acagagggct attgagagat atcaaagcca agactgccta tgaaaagatt | 900 |
| cttctgaatc taaaaacaa atgctctgcg cctcaacaaa aggctctagt tgatcaagtg | 960 |
| atcggaagca gaaatccggg gattgcagac attgaagatc taaccctgct tgctcgtagt | 1020 |
| atggtcgttg ttaggccctc tgtggcaagc aaagtggtgc ttcccataag catttacgcc | 1080 |
| aaaatacctc aactagggtt caatgttgaa gagtactcta tggttgggta cgaagccatg | 1140 |
| gctctttaca atatggcaac acctgtgtcc atattaagaa tgggagatga tgcaaaagat | 1200 |
| aaatcgcaat tattcttcat gtcttgcttc ggagctgcct atgaagacct gagagttttg | 1260 |
| tctgcattga caggcacaga attcaaacct agatcagcat aaaatgcaa gggtttccat | 1320 |
| gttccagcaa aggaacaagt agaaggaatg ggagcagctc tgatgtccat caagctccag | 1380 |
| ttttgggctc aatgaccag atctggggg aacgaagtag gtggagacgg agggtctggc | 1440 |
| caaataagct gcagcccagt gtttgcagtg gaaagaccta ttgctctaag caagcaagct | 1500 |
| gtaaggagaa tgctatcaat gaatattgag ggacgtgatg cagatgtcaa aggaaatcta | 1560 |
| ctcaagatga tgaatgactc aatggctaag aaaaccagtg gaaatgcttt cattgggaag | 1620 |

```
aaaatgtttc aaatatcaga caaaaacaaa accaatccca ttgaaattcc aattaagcag    1680
accatcccca atttcttctt tgggagggac acagcagagg attatgatga cctcgattat    1740
taaagcaaca aaatagacac tatgactgtg attgtttcaa tacgtttgga atgtgggtgt    1800
ttattcttat taaaataaat ataaaaaatg ctgttgtttc tact                    1844
```

<210> SEQ ID NO 6
<211> LENGTH: 1557
<212> TYPE: DNA
<213> ORGANISM: Artificial Sequence
<220> FEATURE:
<223> OTHER INFORMATION: synthetic sequence

<400> SEQUENCE: 6

```
agcagaagca gagcatcttc tcaaaattga agcaaatagg ccgaaaatga acaatgctac     60
cctcaactat acaaacgtta accctatttc tcacatcagg gggagtatta ttatcactat    120
atgtgtcagc ttcactgtca tacttactat attcggatat attgctaaaa ttcccatcaa    180
cagaaattac tgcaccaaca atgccattag attgtgcaaa cgcatcaaat gttcaggctg    240
tgaaccgttc tgcaacaaaa ggggtgacac ttcttctccc agaaccggag tggacatacc    300
cgcgtttatc ttgcccgggc tcaacctttc agaaagcact cctaattagc cctcatagat    360
tcggagagac caaggaaac tcagctccct tgataataag ggaaccttt attgcttgtg     420 gaccaaagga atgcaaacac tttgctctaa cccactatgc agcccaacca ggggatact     480 acaatggaac aagaggagac agaaacaagc tgaggcatct aatttcagtc aaattgggca    540
aaatcccaac agtagaaaac tccattttcc acatggcagc atggagcggg tccgcatgtc    600
atgatggtaa ggaatggaca tatatcggag ttgatggccc tgacaataat gcattgctca    660
aaataaaata tggggaagca tatactgaca cataccattc ctatgcaaac aacatcctaa    720
gaacacaaga aagtgcctgc aattgcatcg gaggaaattg ttatcttatg ataactgatg    780
gctcagcttc aggtgttagt gaatgcagat tcttaaaaat tcgagagggc cgaataataa    840
aagaaatatt tccaacagga agaatacaac atactgaaga atgcacatgc ggatttgcta    900
gcaataaaac catagaatgt gcctgtagag ataacagtta cacagcaaaa agaccctttg    960
tcaaattaaa cgtggagact gatacagcag aaataagatt gatgtgcaca aagacttatt   1020
tggacacccc cagaccagag gatggaagca taactgggcc ttgtgaatct aatgaaggca   1080
aagggagtgg aggcatcaag ggaggatttg tccatcaaag aatggcatcc aagattggaa   1140
ggtggtactc tcgaacgatg tctaaaactg aaaggaaggg gatggggctg tatgtcaagt   1200
ataatggaga cccatgggct gacagtgatg cccttgtttt tagtggagta atggtttcaa   1260
tggaagaacc tggttggtac tcctttggct tcgaaataaa agacaagaaa tgtgatgtcc   1320
cctgtattgg gatagagatg gtacatgatg gtggaaaaga gacttggcac tcagcagcta   1380
cagccattta ctgtttaatg ggctcaggac agctgctgtg gacactgcc acaggtgtta    1440 atatgactct gtaatggagg aatggttgag tctgctctaa accctttgtt cctattttgt   1500
ttgaacaatt gtccttacta aacttaattg tttctgaaaa atgctcttgt tactact       1557
```

<210> SEQ ID NO 7
<211> LENGTH: 1190
<212> TYPE: DNA
<213> ORGANISM: Artificial Sequence
<220> FEATURE:
<223> OTHER INFORMATION: synthetic sequence

<400> SEQUENCE: 7

```
agcagaagca ggcactttct taaaatgtcg ctgtttggag acacaattgc ctacttgctt      60
tcattgacag aagatggaga aggcaaacca gaactagcag aaaaattaca ctgttggttt     120
ggtgggaaag aatttgacct agactctgcc ttagaatgga taaaaaacaa aagatgctta    180
actgatatac aaaaagcact aattggtgcc tctatatgct ttttaaaacc caaagaccag     240
gaaagaaaaa aagagattcat cacagagccc ttatcaggag tgggaacaac agcaacaaaa    300
aagaaaggcc tgattctggc tgagagaaaa atgagaagat gtgtgagctt catgaagca     360
tttgaaatag cagaaggcca tgaaagctca gcgctactat actgtctcat ggtcatgtac    420
ctgaatcctg gaaattattc aatgcaagta aaactaggaa cgctctgtgc tttgtgcgag   480
aaacaagcat cacattcaca cagagctcat agcagagcag cgagatcttc agtgcctgga    540
gtgagacgag aaatgcagat ggtctcagct atgaacacag caaaaacaat gaatggaatg    600
ggaaaaggag aagacgtcca aaagctggca gaagagctgc aaagcaacat tggagtgctg    660
agatctcttg ggcaagtca aaagaatggg gaaggaattg caaggatgt aatggaagtg      720
ctaaagcaga gctctatggg aaattcagct cttgtgaaga aatatctata atgctcgaac    780
catttcagat tctttcaatt tgttcttta tcttatcagc tctccatttc atggcttgga    840
caatagggca tttgaatcaa ataaaaagag gaataaacat gaaaatacga ataaaaagtc    900
caaacaaaga gacaataaac agagaggtat caattttgag acacagttac caaaaagaaa    960
tccaggccaa agaaacaatg aaggaagtac tctctgacaa catggaggta ttgagtgacc   1020
acataataat tgagggcttt tctgccgaag aaataataaa aatgggtgaa acagttttgg   1080
agatagaaga attgcattaa attcaattt tgctgtattt cttactatgc atttaagcaa    1140
attgtaatca atgtcagcaa ataaactgga aaaagtgcgt tgtttctact                1190
```

<210> SEQ ID NO 8
<211> LENGTH: 1097
<212> TYPE: DNA
<213> ORGANISM: Artificial Sequence
<220> FEATURE:
<223> OTHER INFORMATION: synthetic sequence

<400> SEQUENCE: 8

```
agcagaagca gaggatttgt ttagtcactg gcaaacagga aaatggcga acaacatgac       60
cacaacacaa attgaggtgg gtccgggagc aaccaatgcc accataaact ttgaagcagg   120
aattctggag tgctatgaaa ggcttttcatg gcaaagagcc cttgactacc ctggtcaaga    180
ccgcctaaac agactaaaga gaaaattaga gtcaagaata aagactcaca acaaaagtga    240
gcctgaaagt aaaaggatgt cccttgaaga gagaaaagca attggagtaa aaatgatgaa    300
agtactccta tttatggatc cgtctgctgg aattgaaggg tttgagccat actgtatgaa   360
aagttcctca aatagcaact gtacgaaata caattggacc gattacccct caacaccagg    420
gagatgcctt gatgacatag aagaagaacc agaggatgtt gatggcccca ctgaaatagt    480
attaagggac atgaacaaca agatgcgag gcaaaagata aggaggaag taaacactca    540
gaaagaaggg aagttccgtt tgacaataaa aagggatatg cgtaatgtat tgtccttgag    600
agtgttggta acggaacat tcctcaaaca tcccaatgga tacaagtcct tatcaactct    660
gcatagattg aatgtatatg accagagtgg aagcttgtt gctaaacttg ttgctactga    720
tgatcttaca gtggaggatg aagaagatgg ccatcggatc ctcaactcac tcttcgagcg    780
tcttaatgaa ggacattcaa agccaattcg agcagctgaa actgcggtgg gagtcttatc    840
```

-continued

```
ccaatttggt caagagcacc gattatcacc agaagaggga cacaattaga ctggtcacgg    900
aagaacttta tcttttaagt aaaagaattg atgataacat attgttccac aaaacagtaa    960
tagctaacag ctccataata gctgacatgg ttgtatcatt atcattatta gaaacattgt    1020
atgaaatgaa ggatgtggtt gaagtgtaca gcaggcagtg cttgtgaatt taaaataaaa    1080
atcctcttgt tactact                                                   1097
```

<210> SEQ ID NO 9
<211> LENGTH: 29
<212> TYPE: DNA
<213> ORGANISM: Artificial Sequence
<220> FEATURE:
<223> OTHER INFORMATION: synthetic sequence

<400> SEQUENCE: 9
ccgaagttgg gggggagcag aagcggagc                                      29

<210> SEQ ID NO 10
<211> LENGTH: 30
<212> TYPE: DNA
<213> ORGANISM: Artificial Sequence
<220> FEATURE:
<223> OTHER INFORMATION: synthetic sequence

<400> SEQUENCE: 10
ggccgccggg ttattagtag aaacacgagc                                     30

<210> SEQ ID NO 11
<211> LENGTH: 29
<212> TYPE: DNA
<213> ORGANISM: Artificial Sequence
<220> FEATURE:
<223> OTHER INFORMATION: synthetic sequence

<400> SEQUENCE: 11
ccgaagttgg gggggagcag aagcggagc                                      29

<210> SEQ ID NO 12
<211> LENGTH: 30
<212> TYPE: DNA
<213> ORGANISM: Artificial Sequence
<220> FEATURE:
<223> OTHER INFORMATION: synthetic sequence

<400> SEQUENCE: 12
ggccgccggg ttattagtag aaacacgagc                                     30

<210> SEQ ID NO 13
<211> LENGTH: 29
<212> TYPE: DNA
<213> ORGANISM: Artificial Sequence
<220> FEATURE:
<223> OTHER INFORMATION: synthetic sequence

<400> SEQUENCE: 13
ccgaagttgg gggggagcag aagcggtgc                                      29

<210> SEQ ID NO 14
<211> LENGTH: 30
<212> TYPE: DNA
<213> ORGANISM: Artificial Sequence
<220> FEATURE:
<223> OTHER INFORMATION: synthetic sequence

<400> SEQUENCE: 14
ggccgccggg ttattagtag aaacacgtgc                                30

<210> SEQ ID NO 15
<211> LENGTH: 29
<212> TYPE: DNA
<213> ORGANISM: Artificial Sequence
<220> FEATURE:
<223> OTHER INFORMATION: synthetic sequence

<400> SEQUENCE: 15
ccgaagttgg gggggagcag aagcagagc                                 29

<210> SEQ ID NO 16
<211> LENGTH: 30
<212> TYPE: DNA
<213> ORGANISM: Artificial Sequence
<220> FEATURE:
<223> OTHER INFORMATION: synthetic sequence

<400> SEQUENCE: 16
ggccgccggg ttattagtag taacaagagc                                30

<210> SEQ ID NO 17
<211> LENGTH: 29
<212> TYPE: DNA
<213> ORGANISM: Artificial Sequence
<220> FEATURE:
<223> OTHER INFORMATION: synthetic sequence

<400> SEQUENCE: 17
ccgaagttgg gggggagcag aagcagagc                                 29

<210> SEQ ID NO 18
<211> LENGTH: 30
<212> TYPE: DNA
<213> ORGANISM: Artificial Sequence
<220> FEATURE:
<223> OTHER INFORMATION: synthetic sequence

<400> SEQUENCE: 18
ggccgccggg ttattagtag taacaagagc                                30

<210> SEQ ID NO 19
<211> LENGTH: 29
<212> TYPE: DNA
<213> ORGANISM: Artificial Sequence
<220> FEATURE:
<223> OTHER INFORMATION: synthetic sequence

<400> SEQUENCE: 19
ccgaagttgg gggggagcag aagcacagc                                 29

<210> SEQ ID NO 20
<211> LENGTH: 30
<212> TYPE: DNA
<213> ORGANISM: Artificial Sequence
<220> FEATURE:
<223> OTHER INFORMATION: synthetic sequence

<400> SEQUENCE: 20
ggccgccggg ttattagtag aaacaacagc                                30

<210> SEQ ID NO 21
<211> LENGTH: 32

```
<212> TYPE: DNA
<213> ORGANISM: Artificial Sequence
<220> FEATURE:
<223> OTHER INFORMATION: synthetic sequence

<400> SEQUENCE: 21
ccgaagttgg gggggagcag aagcacgcac tt                                     32

<210> SEQ ID NO 22
<211> LENGTH: 33
<212> TYPE: DNA
<213> ORGANISM: Artificial Sequence
<220> FEATURE:
<223> OTHER INFORMATION: synthetic sequence

<400> SEQUENCE: 22
ggccgccggg ttattagtag aaacaacgca ctt                                    33

<210> SEQ ID NO 23
<211> LENGTH: 32
<212> TYPE: DNA
<213> ORGANISM: Artificial Sequence
<220> FEATURE:
<223> OTHER INFORMATION: synthetic sequence

<400> SEQUENCE: 23
ccgaagttgg gggggagcag aagcagagga tt                                     32

<210> SEQ ID NO 24
<211> LENGTH: 33
<212> TYPE: DNA
<213> ORGANISM: Artificial Sequence
<220> FEATURE:
<223> OTHER INFORMATION: synthetic sequence

<400> SEQUENCE: 24
ggccgccggg ttattagtag taacaagagg att                                    33

<210> SEQ ID NO 25
<211> LENGTH: 22
<212> TYPE: DNA
<213> ORGANISM: Artificial Sequence
<220> FEATURE:
<223> OTHER INFORMATION: synthetic sequence

<400> SEQUENCE: 25
ctcaatttgt gttgtggtca tg                                                22

<210> SEQ ID NO 26
<211> LENGTH: 32
<212> TYPE: DNA
<213> ORGANISM: Artificial Sequence
<220> FEATURE:
<223> OTHER INFORMATION: synthetic sequence

<400> SEQUENCE: 26
tggaggatga agaagatggc catcggatcc tc                                     32
```

LIVE ATTENUATED INFLUENZA B VIRUS COMPOSITIONS METHODS OF MAKING AND USING THEREOF

CROSS-REFERENCE TO RELATED APPLICATIONS

This application is a National Phase application under 35 U.S.C. 371 of PCT/CN2018/115938, Nov. 16, 2018, which is hereby incorporated herein by reference in its entirety.

FIELD OF THE INVENTION

The present invention is generally in the field of live attenuated influenza virus (LAIV) B and immunogenic compositions including LAIVB, and methods of using such compositions for inducing an immune response to antigen(s) encoded by the viral genome.

BACKGROUND OF THE INVENTION

The influenza viruses are classified into types A, B, and C on the basis of differences in viral nucleoprotein (NP) and matric protein. Type A viruses are further subdivided different subtupes according to their envelope glycoproteins with haemagglutinin (HA) or neuraminidase (NA) activity. There are 18 different hemagglutinin subtypes and 11 different neuraminidase subtypes. (H1 through H18 and N1 through N11 respectively.) Influenza B viruses are not divided into subtypes, but can be further broken down into lineages and strains. Currently circulating influenza B viruses belong to one of two lineages: B/Yamagata and B/Victoria. Influenza B and C viruses mainly affect humans, whereas influenza A viruses infect a range of mammalian and avian species. Only type A and B cause human disease of any concern. Influenza occurs all over the world, with an annual global attack rate estimated at 5-10% in adults and 20-30% in children (Thompsomn, et al., *JAMA* 292, 1333-1340 (2004); WOrld Health Organization Influenza (seasonal) fact sheet. World Health Organization (online) http://www.who.int/mediacentre/factsheets/fs211/en (2014)), leading 2 to 5 million severe disease and as many as 650,000 cases are fatal each year (Iuliano et al., Lancet 391, 1285-1300 (2018); Whord Health Organization, 2016 Influenza (seasonal) fact sheet 211. www.who.int./mediacentre/factsheets/fs211/en). Vaccination with flu vaccine is considered to be the most effective way to alleviate disease burden and mortality caused by seasonal influenza, as well as to prevent future pandemics in humans.

There are currently three types of inactivated vaccines available, the whole virus vaccines, split virus vaccines, and subunit vaccines. In split virus vaccines, the virus has been disrupted by a detergent. In subunit vaccines, HA and NA have been further purified by removal of other viral components. Live, attenuated influenza vaccines have been based on cold-adapted and temperature-sensitive variant vaccine virus strains that replicate well in the nasopharynx of upper respiratory tract but poorly in the lower respiratory tract (Jin, e t al. *Curr Top Microbiol Immunol* 386, 181-204 (2015)). Current licensed flu vaccines are either trivalent (three-component) or quadrivalent (four-component). Trivalent influenza vaccines composed of antigens derived from two influenza A, H1N1 and H3N2 subtype viruses, and either strain of influenza B virus from Victoria or Yamagata lineage based on surveillance data of World Health Origination (WHO) influenza network laboratories. A quadrivalent flu vaccine was first licensed in 2012 in the US and made available in the 2013-2014 flu season. Quadrivalent vaccines which contain antigens for protection against influenza A H1N1, H3N2 subtypes virus and both lineages of flu B viruses were recommended in 2013 by WHO, but leaving each country/state to decide to use either trivalent or quadrivalent vaccine. Flu vaccine strains are selected annually according to the data collected by the surveillance program from collaborating network laboratories of WHO for influenza vaccine. There is disparity of illness among humans caused by different strains of influenza virus, with influenza B more common in children and H3N2 more among the elderly (Caini, et al., *BMC Infect Dis* 18, 269 (2018)). While it was previously thought that influenza B virus mainly causes diseases for older children, it has been noticed that there is a gradually change of the epidemic pattern of influenza B virus with diseases burden in all age groups since 2005 (Glezen, et al., *Am J Public Health* 103, e43-51 (2013)). Since influenza B virus is only circulating in humans, an effective vaccine influenza B virus may eventually achieve eradication of flu B virus from humans. Like the circulation of H1N1 and H3N2 subtypes, two antigenic distinct flu B virus, Yamagata and Victoria lineages, circulate in humans alternatively, with the trend difficult to predict correctly each year. Current seasonal flu vaccines are suboptimal for the variable nature of circulating flu viruses each season. Further, although live attenuated influenza virus (LAIV) vaccine has advantages because it induces both humoral and cellular immunity, the current available LAIV vaccine is only licensed for use in 2-49 age group, due to the safety concern in young children and uncertain efficacy in the older age group. The NS1 protein of influenza virus has multiple functions and is a determinant of virulence, making its deletion an attractive target strategy for live vaccines. However, deletion of NS1 severely affects virus replication, making it difficult to produce high titers of attenuated virus for vaccine applications.

Talon, et al., *PNAS*, 97(8):4309-1314 (2000) disclose the growth characteristics of influenza B/201 and B/234 viral variants. Influenza B/201 and influenza B/AWBY/234 (B/234) viruses are laboratory variants of influenza B/Yamagata/1/73 that contain alterations in the NS1 ORF as compared with the NS1 ORF of wild-type influenza B/Yamagata. Nucleotide deletions in the NS gene of either B/201 or B/234 create frame shifts that result in the generation of shortened NS1 proteins. The influenza B/201 and B/234 viral NS1 proteins contain, respectively, 110 and 89 amino acids corresponding to the N terminus of the B/Yamagata viral NS1 protein. Both B/201 and B/234 viruses grow in 6-day-old eggs albeit to lower titers than B/Yamagata virus. However, whereas B/Yamagata grew equally well in 8-day-old eggs, growth of the other two viruses was markedly reduced in embryos of this age. Talon, et al., *PNAS*, 97(8): 4309-1314 (2000).

Hai, et al., *J. Virol.*, 82(21):10580-10590 (2008) discloses influenza B virus truncated mutants of influenza B/Yamagata/88. For the generation of the different NS1 truncation mutants, a total of three influenza B/Yamagata/88 virus NS1 mutants, deltaNS1, NS1-80, and NS1-110, were constructed by using the pDZ plasmid. The coding region of the influenza B/Yamagata/88 virus NS1 gene is 846 nucleotides long (corresponding to 282 amino acids). Deletions and sequential truncations corresponding to the NS1 C terminus were made in this segment, resulting in three constructs encoding amino acids 1 to 16 (deltaNS1), 1 to 80 (NS1-80), or 1 to 110 (NS1-110) of the NS1 protein. The open reading frame of the NEP (nuclear export protein) was not altered in these constructs. According to Hai et al., the mutant viruses exhibited lower peak titers than the rWT virus in IFN-deficient Vero cells as well as in MDCK cells, although the deltaNS1 virus did grow more efficiently in Vero cells than in MDCK cells.

Pica et al., *J. Virol.*, 86(19):10293-10301 (2012) discloses recombinant viruses expressed either the full-length NS1 protein (wild-type [WT] PR8) or the first 126 amino acids (NS1-126).

Novel strategies to develop more effective vaccine against influenza B virus with properties to provide broad cross protective activity are necessary.

It is an object of the present invention to provide a safer and more effective live attenuated influenza B vaccine.

It is also an object of the present invention to provide methods of generating mutant influenza B viruses with improved ability to replication in influenza vaccine producing systems.

It is a further object of the present invention to provide methods of replicating live attenuated influenza B virus with high titre values useful for vaccine applications.

It is a further object of the present invention to provide methods of eliciting an immune response against an influenza virus B in a mammal.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY OF THE INVENTION

A Live attenuated influenza virus (LAIV) B "LAIVB") from Victoria lineage is provided, with a deletion of the viral virulence element, the NS1 (non-structural protein 1), LAVIB/DelNS1. The LAIVB/DelNS1 additionally includes adaptive nucleotide mutations (AM) in segments 3 and 5-7 as follows: PA(T210C), NA T(1424C), NP(C182T) and M (A281G). The mutations are highlighted in the DNA sequences. The LAIB/DelNS1 with adaptive mutations is referred to herein as AM/LAVIB/DelNS1. The AM/LAVIB/DelNS1 preferably, is not able to replicate in interferon-competent cells, for example, A549 cells, and preferably replicates at low temperatures such as temperatures below 37° C., more preferably between 30 and 33° C. and most preferably, at about 33° C. In a particularly preferred embodiment, the disclosed LAIVB is characterized in that it replicated poorly in MDCK cells at 37° C., when compared to its replication at 33° C. in the MDCK cells. In a particularly preferred embodiment, the mutated LAIVB/DelLNS1 is able to replicate at levels comparable to wild type influenza virus of the same strain, in a vaccine producing system for example, eggs, or MDCK cells. For example, the LAIVB/DelLNS1 is able to replicate at levels>$10^7$ plaque forming units (pfu/ml) for example, between $10^7$-$10^8$ pfu/ml.

Also disclosed are methods for making LAIVB with a deletion of the viral virulence element, the NS1 protein and adaptive mutations that allows growth of the mutated strain in vaccine producing systems such as eggs and MDCK cells (i.e., AM/LAVIB/DelNS1). Preferred virus strains include B/Yamagata and B/Victoria. The preferred adaptive mutations are PA(T210C), NA T(1424C), NP(C182T) and M (A281G) mutations in a Victoria strain. The methods include (a) generating influenza B virus with deletion of the coding region of the NS1 coding region by transfecting the DelNS1 influenza B virus into one or more vaccine producing cells (b) rescuing LAVIB/DelNS1 and (c) passaging rescued virus in one or more vaccine producing cells until viral titer is stabilized, to obtain AM/LAVIB/DelNS1.

The disclosed methods preferably include reverse genetics. In particularly preferred embodiments, plasmids containing the deleted NS1 segment (DelNS1) and the other seven genome segments derived from an influenza B virus strain are transfected into 293T/MDCK cell mixture. Rescued virus is passaged in MDCK cells until virus titer is stabilized, with virus titer maintains without meaningful change for three consecutive passages. As used herein, without meaningful change refers to changes including no change or no statistically significant change. Whole sequence of growth-adapted DelNS1 influenza B virus was analyzed and acquired mutations were identified as presented in FIG. 1B. The virus is sequenced to determine adaptive mutations.

Pharmaceutical compositions are also provided. The pharmaceutical compositions include the disclosed immunogenic AM/LAVIB/DelNS1 produced according to the disclosed methods. The pharmaceutical compositions typically include an effective amount of a virus to induce an immune response in subject in need thereof when administered to the subject. The pharmaceutical compositions can include additional agents, for example adjuvants to enhance the immune response. In some embodiments, the pharmaceutical compositions do not include an adjuvant. In one embodiment, the composition include an effective mount of a AM/LAVIB/DelNS1 from influenza of the Victoria lineage, with an NS1 deletion and mutations in segments 3, and 5-7 as follows: PA(T210C), NA T(1424C), NP(C182T) and M (A281G).

Methods of treating a subject in need thereof by administering the pharmaceutical composition to the subject are also provided. The methods can be vaccine protocols. Thus, in some embodiments, the subject is administered the composition to provide prophylactic or therapeutic protection against the virus itself (e.g., autologous antigen(s)) alone or in combination with protection against an infection from another virus, preferably, another influenza virus A or B strain. The disclosed AM/LAVIB/DelNS1 generated according to the methods disclosed here are administered to a mammal in need thereof by subcutaneous (s.c.), intradermal (i.d.), intramuscular (i.m.), intravenous (i.v.), oral, or intranasal administration; or by injection or by inhalation. In other aspects, the strain is administered intranasally. The AM/LAVIB/DelNS1 is administrated to a mammal in need of protective immunity against the influenza infection.

BRIEF DESCRIPTION OF THE DRAWINGS

FIGS. 1A and 1B show generation and characterization of DelNS1 influenza B live attenuated virus vaccine. FIG. 1A is an illustration of generation of DelNS1-8308B influenza B virus by reverse genetics. pHW2000 plasmids containing the DelNS1 segment and the other seven genome segments derived from B/Hong Kong/8038/2011 (Victoria) virus were transfected into 293T/MDCK cell mixture. Rescued virus was passaged in MDCK cells until virus titer was stabilized. FIG. 1B. shows identified adaptive mutations in growth adapted DelNS1-8308B influenza B virus. Four mutations in PA(T210C), NA T(1424C), NP(C182T) and M (A281G) were identified.

(FIGS. 2A and 2C) and 33° C. degrees respectively (FIGS. 2B and 2D). DelNS1 flu B virus is not able to replicate in A549 cells and poorly replicate in MDCK cells at 37° C. degree. However, DelNS1 flu B virus is able to replicate at levels comparable to wild type flu B virus at 33° C. in MDCK cells.

DETAILED DESCRIPTION OF THE INVENTION

I. Definitions

Materials

Figure 2A:
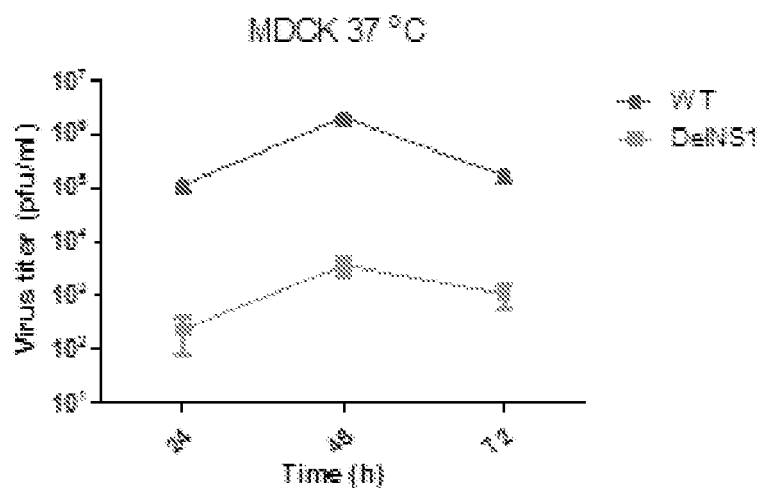
FIGS. 2A-2D show growth kinetics of DelNS1 virus were estimated in MDCK (FIGS. 2A and 2B) and A549 (FIGS. 2C and 2D) cells at 37° C.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if an aptamer is disclosed and discussed and a number of modifications that can be made to a number of molecules or compositions including the aptamer are discussed, each and every combination and permutation of the aptamer and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. Further, each of the materials, compositions, components, etc. contemplated and disclosed as above can also be specifically and independently included or excluded from any group, subgroup, list, set, etc. of such materials. These concepts apply to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

As used herein, the term "adjuvant" refers to a compound or mixture that enhances an immune response.

As used herein, "attenuated" refers to refers to procedures that weaken an agent of disease (a pathogen). An attenuated virus is a weakened, less vigorous virus. A vaccine against a viral disease can be made from an attenuated, less virulent strain of the virus, a virus capable of stimulating an immune response and creating immunity but not causing illness or less severe illness. Attenuation can be achieved by chemical treatment of the pathogen, through radiation, or by genetic modification, using methods known to those skilled in the art. Attenuation may result in decreased proliferation, attachment to host cells, or decreased production or strength of toxins.

As used herein, "autologous" means derived from self.

The term "child" is meant to be a person or a mammal between 0 months and 18 years of age and "young child" refers to a child<5 yrs. old.

As used herein, the term "effective amount" or "therapeutically effective amount" means a dosage sufficient to treat, inhibit, or alleviate one or more symptoms of a disease state being treated or to otherwise provide a desired pharmacologic effect. The precise dosage will vary according to a variety of factors such as subject-dependent variables (e.g., age, immune system health, etc.), the disease, and the age of the subject.

As used herein, the term "gene" refers to a nucleic acid (e.g., DNA or RNA) sequence that including coding sequences necessary for the production of a polypeptide, RNA (e.g., including but not limited to, mRNA, tRNA and rRNA) or precursor. The polypeptide, RNA, or precursor can be encoded by a full length coding sequence or by any portion thereof. The term also encompasses the coding region of a structural gene and the sequences located adjacent to the coding region on both the 5' and 3' ends for a distance of about 1 kb on either end such that the gene corresponds to the length of the full-length mRNA. The term "gene" encompasses both cDNA and genomic forms of a gene, which may be made of DNA, or RNA. A genomic form or clone of a gene may contain the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

The term "immunogenic composition" or "composition" means that the composition can induce an immune response and is therefore antigenic. By "immune response" means any reaction by the immune system. These reactions include the alteration in the activity of an organism's immune system in response to an antigen and can involve, for example, antibody production, induction of cell-mediated immunity, complement activation, or development of immunological tolerance.

The term "nasal administration" refers to any form of administration whereby an active ingredient is propelled or otherwise introduced into the nasal passages of a subject so that it contacts the respiratory epithelium of the nasal cavity, from which it is absorbed into the systemic circulation. Nasal administration can also involve contacting the olfactory epithelium, which is located at the top of the nasal cavity between the central nasal septum and the lateral wall of each main nasal passage. The region of the nasal cavity immediately surrounding the olfactory epithelium is free of airflow. Thus, specialized methods must typically be employed to achieve significant absorption across the olfactory epithelium.

The terms "oral", "enteral", "enterally", "orally", "non-parenteral", "non-parenterally", and the like, refer to administration of a compound or composition to an individual by a route or mode along the alimentary canal. Examples of "oral" routes of administration of a composition include, without limitation, swallowing liquid or solid forms of a vaccine composition from the mouth, administration of a vaccine composition through a nasojejunal or gastrostomy tube, intraduodenal administration of a vaccine composition, and rectal administration, e.g., using suppositories that release a live bacterial vaccine strain described herein.

The term "mammal" as used herein includes both humans and non-humans and include but is not limited to humans, non-human primates, canines, felines, murines, bovines, equines, and porcines.

The term "topical administration" refers to the application of a pharmaceutical agent to the external surface of the skin or the mucous membranes (including the surface membranes of the nose, lungs and mouth), such that the agent crosses the external surface of the skin or mucous membrane and enters the underlying tissues. Topical administration can result in a limited distribution of the agent to the skin and surrounding tissues or, when the agent is removed from the treatment area by the bloodstream, systemic distribution of the agent. In a preferred form, the agent is delivered by transdermal delivery, e.g., using a transdermal patch. Transdermal delivery refers to the diffusion of an agent across the skin (stratum corneum and epidermis), which acts as a barrier few agents are able to penetrate. In contrast, the dermis is permeable to absorption of many solutes and drugs, and topical administration therefor occurs more readily through skin which is abraded or otherwise stripped of the epidermis to expose the dermis. Absorption through intact skin can be enhanced by combining the active agent with an oily vehicle (e.g., creams, emollients, penetration enhancers, and the like, as described, e.g., in Remington's Pharmaceutical Sciences, current edition, Gennaro et al., eds.) prior to application to the skin (a process known as inunction).

As used herein, the term "peptide" refers to a class of compounds composed of amino acids chemically bound together. In general, the amino acids are chemically bound together via amide linkages (CONH); however, the amino acids may be bound together by other chemical bonds known in the art. For example, the amino acids may be bound by amine linkages. Peptide as used herein includes oligomers of amino acids and small and large peptides, including polypeptides.

As used herein "recombinant DNA" a refers to DNA molecules that is extracted from different sources and chemically joined together; for example DNA including a gene from one source may be recombined with DNA from another source. Recombinant DNA can be all heterologous DNA or a combination of homologous and heterologous DNA. The recombinant DNA can be integrated into and expressed from a cell's chromosome, or can be expressed for an extra-chromosomal array such as a plasmid.

As used herein, a "variant," "mutant," or "mutated" polynucleotide or polypeptide contains at least one polynucleotide or polypeptide sequence alteration as compared to the polynucleotide or polypeptide sequence of the corresponding wild-type or parent polynucleotide or polypeptide. Mutations may be natural, deliberate, or accidental. Mutations include substitutions, deletions, and insertions.

II. Compositions

Figure 3A:
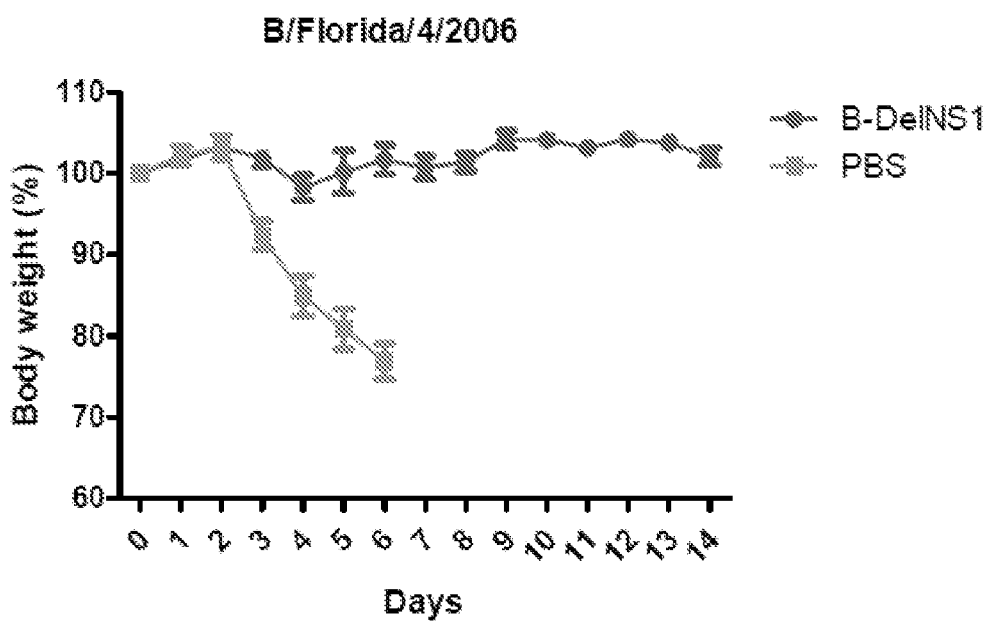
FIGS. 3A and 3B show protection following lethal challenge in mouse with DelNS1 Flu B vaccine, measured in terms of body weight following vaccination. Mice were vaccinated with DelNS1 Flu B vaccine (Victoria lineage, $2\times10^6$ pfu) ONCE through nasal drop. After three weeks, vaccinated mice were subsequently challenged with either one of mouse adapted flu B viruses, B/Florida/4/2006 (Yamagata lineage, $5\times10^5$ $TCID_{50}$) (FIG. 3A) or B/Brisbane/60/2008 (Victoria lineage, $5\times10^6$ $TCID_{50}$) (FIG. 3B). Body weight and survival rate of the mice were recorded for 2 weeks.
Figure 3B:
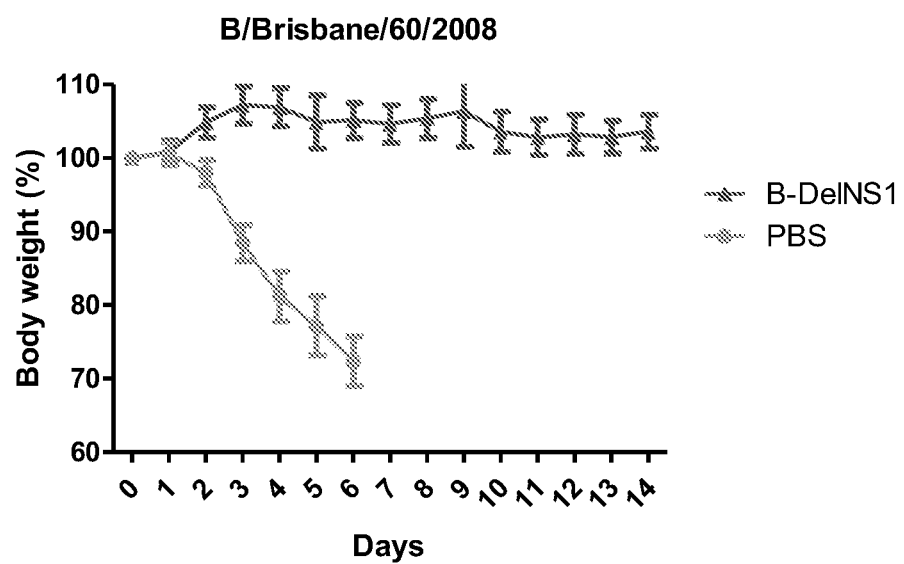

Immunogenic compositions including live attenuated influenza B (LAIVB) virus are provided. The compositions are immunogenic in that they can be used to elicit an immune response against one or more antigens encoded by the LAIVB. The LAIVB has improved safety due to deletion of the coding region of the NS1 segment (DelNS1) and adaptive mutations (AM) which improve its growth in vaccine producing systems. Influenza B viruses with these combinations of mutations are referred to herein as AM/LAVIB/DelNS1. The examples demonstrate that AM/LAVIB/DelNS1 virus is not virulent to mice, even when challenged with the highest dose of virus (FIGS. 3A and 3B). The AM/LAVIB/DelNS1 can be included in a formulation for administration, in a carrier, and in some embodiments, in combination with an adjuvant. The adjuvant can serve as the carrier. In some embodiments, immunogenic compositions containing the disclosed AM/LAVIB/DelNS1 do not include an adjuvant.

A. Live Attenuated Virus

The influenza B virus genomes each comprise eight negative-sense, single-stranded viral RNA (vRNA) segments. The smallest vRNA segment of both viruses encodes the non-structural NS1 protein. Influenza B virus expresses from an unspliced transcript of the viral NS segment a 281-amino-acid nonstructural protein termed NS1-B. The disclosed LAIVB preferably include a complete deletion of the coding region for NS1 from the LAIVB genome. The AM/LAVIB/DelNS1 can be of the Yamagata or Victoria lineage. During 1988-1989 two highly distinct antigenic variants of influenza type B were recognized in hemagglutination-inhibition tests with post infection ferret serum. These viruses were antigenically related to either B/Victoria/2/87, the most recent reference strain, or B/Yamagata/16/88, a variant that was isolated in Japan in May 1988. All influenza B viruses isolated in the United States during an epidemic in the winter of 1988-1989 were antigenically related to B/Victoria/2/87. Different strains of influenza B virus are disclosed in the Influenza Research Database. Zhang, et al., *Nucleic Acids Research*, Volume 45(D1): D466-D474, 2017.

The eight segments of influenza B viruses (and are numbered in order of decreasing length (TABLE 1). Segments 1, 3, 4, and 5 encode just one protein per segment: the PB2, PA, HA and NP proteins.

TABLE 1

Segments of Influenza B virus and their encoded proteins

| Segment | Encoded Protein | Protein Function |
|---|---|---|
| 1 (SEQ ID NO: 1) | PB2 | Polymerase subunit; mRNA cap recognition |
| 2 (SEQ ID NO: 2) | PB1 | Polymerase subunit; RNA elongation, endonuclease activity |
| 3 (SEQ ID NO: 3) | PA | Polymerase subunit; protease activity |
| 4 (SEQ ID NO: 4) | HA | Surface glycoprotein; major antigen, receptor binding and fusion activities |
| 5 (SEQ ID NO: 5) | NP | RNA binding protein; nuclear import regulation |
| 6 (SEQ ID NO: 6) | NA | Surface glycoprotein; sialidase activity, virus release |
|  | NB | an integral membrane protein corresponding to the influenza A virus M2 protein |
| 7 (SEQ ID NO: 7) | M1 | Matrix protein; vRNP interaction, RNA nuclear export regulation, viral budding |
| 8 (SEQ ID NO: 8) | NS1 | Interferon antagonist protein; regulation of host gene expression |
|  | NEP/NS2 | Nuclear export of RNA |

All influenza viruses encode the polymerase subunit PB1 on segment 2.

The mutated influenza B virus disclosed herein includes an NS1 deletion, and the following mutations: PA(T210C), NA(T1424C), NP (C182T) and M (A281G). The disclosed LAIV B can be readily distinguished from viruses described in U.S. Pat. No. 8,592,196.

Similar mutations can be introduced into the respective segments for other influenza B virus; the segment sequences which are publicly disclosed. For example, the GenBank accession number for various influenza B virus segment 7 nucleotide sequence are: DQ792908.1 (Influenza B virus (B/Lee/40) cold-adapted M1 protein (M1) and BM2 protein (BM2) genes, complete cds); M20175.1 (Influenza B/Ann Arbor/1/66 (cold-adapted) membrane protein M1 (seg 7) RNA, complete cds); CY018758.1 (Influenza B virus (B/Victoria/02/1987) segment 7, complete sequence); CY018686.1 (Influenza B virus (B/Hong Kong/1434/2002) segment 7, complete sequence.

B. Adjuvants

The disclosed LAIV can be administered in conjunction with other immunoregulatory agents, including adjuvants. Useful adjuvants but are not limited to, one or more set forth below:

Mineral Containing Adjuvant Compositions include mineral salts, such as aluminum salts and calcium salts. Exemplary mineral salts include hydroxides (e.g., oxyhydroxides), phosphates (e.g., hydroxyphosphates, orthophosphates), sulfates, and the like or mixtures of different mineral compounds (e.g., a mixture of a phosphate and a hydroxide adjuvant, optionally with an excess of the phosphate), with the compounds taking any suitable form (e.g., gel, crystalline, amorphous, and the like), and with adsorption to the salt(s) being preferred. The mineral containing compositions can also be formulated as a particle of metal salt (WO/0023105). Aluminum salts can be included in compositions of the invention such that the dose of $Al^{3+}$ is between 0.2 and 1.0 mg per dose.

Oil-Emulsion Adjuvants suitable for use as adjuvants in the invention can include squalene-water emulsions, such as MF59 (5% Squalene, 0.5% Tween 80, and 0.5% Span 85, formulated into submicron particles using a microfluidizer). See, e.g., WO90/14837. and, Podda, *Vaccine* 19: 2673-2680, 2001. Additional adjuvants for use in the compositions are submicron oil-in-water emulsions. Examples of submicron oil-in-water emulsions for use herein include squalene/water emulsions optionally containing varying amounts of MTP-PE, such as a submicron oil-in-water emulsion containing 4-5% w/v squalene, 0.25-1.0% w/v Tween 80 (polyoxyethylenesorbitan monooleate), and/or 0.25-1.0% Span 85 (sorbitan trioleate), and, optionally, N-acetylmuramyl-L-alanyl-D-isogluatminyl-L-alanine-2-(1'-2'-dipalmitoyl-s-n-glycero-3-huydroxyphosphophoryloxy)-ethylamine (MTP-PE), for example, the submicron oil-in-water emulsion known as "MF59" (International Publication No. WO90/14837; U.S. Pat. Nos. 6,299,884 and 6,451,325, incorporated herein by reference in their entirety. MF59 can contain 4-5% w/v Squalene (e.g., 4.3%), 0.25-0.5% w/v Tween 80, and 0.5% w/v Span 85 and optionally contains various amounts of MTP-PE, formulated into submicron particles using a microfluidizer such as Model 110Y microfluidizer (Microfluidics, Newton, Mass.). For example, MTP-PE can be present in an amount of about 0-500 μg/dose, or 0-250 μg/dose, or 0-100 μg/dose. Submicron oil-in-water emulsions, methods of making the same and immunostimulating agents, such as muramyl peptides, for use in the compositions, are described in detail in International Publication No. WO90/14837 and U.S. Pat. Nos. 6,299,884 and 6,451,325.

Complete Freund's adjuvant (CFA) and incomplete Freund's adjuvant (IFA) can also be used as adjuvants in the invention.

Saponin Adjuvant Formulations can also be used as adjuvants in the invention. Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations can include purified formulations, such as QS21, as well as lipid formulations, such as Immunostimulating Complexes (ISCOMs; see below). Saponin compositions have been purified using High Performance Thin Layer Chromatography (HPLC) and Reversed Phase High Performance Liquid Chromatography (RP-HPLC). Specific purified fractions using these techniques have been identified, including QS7, QS17, QS18, QS21, QH-A, QH-B and QH-C. A method of production of QS21 is disclosed in U.S. Pat. No. 5,057,540. Saponin formulations can also comprise a sterol, such as cholesterol (see WO96/33739). Combinations of saponins and cholesterols can be used to form unique particles called ISCOMs. ISCOMs typically also include a phospholipid such as phosphatidylethanolamine or phosphatidylcholine. Any known saponin can be used in ISCOMs. For example, an ISCOM can include one or more of Quil A, QHA and QHC. ISCOMs are described in EP0109942, WO96/11711, and WO96/33739. Optionally, the ISCOMS can be devoid of additional detergent. See WO00/07621. A description of the development of saponin based adjuvants can be found at Barr, et al., "ISCOMs and other saponin based adjuvants", *Advanced Drug Delivery Reviews* 32: 247-27, 1998. See also Sjolander, et al., "Uptake and adjuvant activity of orally delivered saponin and ISCOM vaccines", *Advanced Drug Delivery Reviews* 32: 321-338, 1998.

Virosomes and Virus Like Particles (VLPs) can also be used as adjuvants. These structures generally contain one or more proteins from a virus optionally combined or formulated with a phospholipid. They are generally non-pathogenic, non-replicating and generally do not contain any of the native viral genome. The viral proteins can be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, QB-phage (such as coat proteins), GA-phage, fr-phage, AP205 phage, and Ty (such as retrotransposon Ty protein p1).

Bacterial or Microbial Derivatives useful as adjuvants include: (i) Non-Toxic Derivatives of Enterobacterial Lipopolysaccharide (LPS); (ii) lipid derivatives, (iii) immunostimulatory oligonucleotides and ADP-Ribosylating Toxins and Detoxified Derivatives Thereof, (iv) ADP-Ribosylating Toxins and Detoxified Derivatives Thereof. Examples of Non-Toxic Derivatives of LPS Monophosphoryl lipid A (MPL) and 3-O-deacylated MPL (3 dMPL). 3 dMPL is a mixture of 3 De-O-acylated monophosphoryl lipid A with 4, 5 or 6 acylated chains. An example of a "small particle" form of 3 De-O-acylated monophosphoryl lipid A is disclosed in EP 0 689 454. Such "small particles" of 3 dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives e.g., RC-529 (Johnson et al., *Bioorg Med Chem Lett*, 9: 2273-2278, 1999). Examples of lipid A derivatives can include derivatives of lipid A from *Escherichia coli* such as OM-174. OM-174 is described for example in Meraldi et al., "OM-174, a New Adjuvant with a Potential for Human Use, Induces a Protective Response with Administered with the Synthetic C-Terminal Fragment 242-310 from the circumsporozoite protein of *Plasmodium berghei*", *Vaccine* 21: 2485-2491, 2003; and Pajak, et al., "The Adjuvant OM-174 induces both the migration and maturation of murine dendritic cells in vivo", *Vaccine* 21: 836-842, 2003. Examples of immunostimulatory oligonucleotides nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory.

The CpG's can include nucleotide modifications/analogs such as phosphorothioate modifications and can be double-stranded or single-stranded. Optionally, the guanosine can be replaced with an analog such as 2'-deoxy-7-deazaguanosine. See Kandimalla, et al., "Divergent synthetic nucleotide motif recognition pattern: design and development of potent immunomodulatory oligodeoxyribonucleotide agents with distinct cytokine induction profiles", *Nucleic Acids Research* 31: 2393-2400, 2003; WO02/26757 and WO99/62923 for examples of analog substitutions. The adjuvant effect of CpG oligonucleotides is further discussed in Krieg, *Nature Medicine* (2003) 9(7): 831-835; McCluskie, et al., *FEMS Immunology and Medical Microbiology* (2002) 32:179-185; WO98/40100; U.S. Pat. Nos. 6,207,646; 6,239,116 and 6,429,199. The CpG sequence can be directed to Toll-like receptor (TLR9), such as the motif GTCGTT or TTCGTT. See Kandimalla, et al., "Toll-like receptor 9: modulation of recognition and cytokine induction by novel synthetic CpG DNAs", *Biochemical Society Transactions* (2003) 31 (part 3): 654-658. The CpG sequence can be specific for inducing a Th1 immune response, such as a CpG-A ODN, or it can be more specific for inducing a B cell response, such a CpG-B ODN. CpG-A and CpG-B ODNs are discussed in Blackwell, et al., *J. Immunol.* 170: 4061-4068, 2003; Krieg, *TRENDS in Immunology* 23: 64-65, 2002, and WO01/95935. In some aspects, the CpG oligonucleotide can be constructed so that the 5' end is accessible for receptor recognition. Optionally, two CpG oligonucleotide sequences can be attached at their 3' ends to form "immunomers". See, for example, Kandimalla, et al., *BBRC* 306: 948-95, 2003; Kandimalla, et al., *Biochemical Society Transactions* 31: 664-658, 2003; Bhagat et al., "*BBRC* 300: 853-861, 2003, and WO03/035836. Bacterial ADP-ribosylating toxins and detoxified derivatives thereof can be used as adjuvants in the invention. For example, the toxin can be derived from *E. coli* (i.e., *E. coli* heat labile enterotoxin (LT)), cholera (CT), or pertussis (PTX). The use of detoxified ADP-ribosylating toxins as mucosal adjuvants is described in WO95/17211 and as parenteral adjuvants in WO98/42375. In some aspects, the adjuvant can be a detoxified LT mutant such as LT-K63, LT-R72, and LTR192G. The use of ADP-ribosylating toxins and detoxified derivatives thereof, particularly LT-K63 and LT-R72, as adjuvants can be found in the following references, each of which is specifically incorporated by reference herein in their entirety: Beignon, et al., *Infection and Immunity* 70: 3012-3019, 2002; Pizza, et al., *Vaccine* 19: 2534-2541, 2001; Pizza, et al., Int. J. Med. Microbiol 290: 455-461, 2003; Scharton-Kersten et al., *Infection and Immunity* 68: 5306-5313, 2000; Ryan et al., *Infection and Immunity* 67: 6270-6280, 2003; Partidos et al., *Immunol. Lett.* 67: 09-216, 1999; Peppoloni et al., *Vaccines* 2: 285-293, 2003; and Pine et al., *J. Control Release* 85: 263-270, 2002.

Bioadhesives and mucoadhesives can also be used as adjuvants in the invention. Suitable bioadhesives can include esterified hyaluronic acid microspheres (Singh et al., *J. Cont. Rel.* 70:267-276, 2001) or mucoadhesives such as cross-linked derivatives of poly(acrylic acid), polyvinyl alcohol, polyvinyl pyrollidone, polysaccharides and carboxymethylcellulose. Chitosan and derivatives thereof can also be used as adjuvants in the invention disclosed for example in WO99/27960.

Adjuvant Microparticles: Microparticles can also be used as adjuvants. Microparticles (i.e., a particle of about 100 nm to about 150 µm in diameter, or 200 nm to about 30 µm in diameter, or about 500 nm to about 10 µm in diameter) formed from materials that are biodegradable and/or non-toxic (e.g., a poly(alpha-hydroxy acid), a polyhydroxybutyric acid, a polyorthoester, a polyanhydride, a polycaprolactone, and the like), with poly(lactide-co-glycolide) are envisioned, optionally treated to have a negatively-charged surface (e.g., with SDS) or a positively-charged surface (e.g., with a cationic detergent, such as CTAB).

Examples of liposome formulations suitable for use as adjuvants are described in U.S. Pat. Nos. 6,090,406, 5,916, 588, and EP 0 626 169.

Additional adjuvants include polyoxyethylene ethers and polyoxyethylene esters. WO99/52549. Such formulations can further include polyoxyethylene sorbitan ester surfactants in combination with an octoxynol (WO 01/21207) as well as polyoxyethylene alkyl ethers or ester surfactants in combination with at least one additional non-ionic surfactant such as an octoxynol (WO 01/21152). In some aspects, polyoxyethylene ethers can include: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, or polyoxyethylene-23-lauryl ether.

PCPP formulations for use as adjuvants are described, for example, in Andrianov et al., *Biomaterials* 19: 109-115, 1998.1998. Examples of muramyl peptides suitable for use as adjuvants in the invention can include N-acetyl-muramyl-L-threonyl-D-isoglutamine (thr-MDP), N-acetyl-normuramyl-1-alanyl-d-isoglutamine (nor-MDP), and N-acetyl-muramyl-1-alanyl-d-isoglutaminyl-1-alanine-2-(1'-2'-dipalmitoyl-s-n-glycero-3-hydroxyphosphoryloxy)-ethylamine MTP-PE). Examples of imidazoquinolone compounds suitable for use as adjuvants in the invention can include Imiquimod and its homologues, described further in Stanley, "Imiquimod and the imidazoquinolones: mechanism of action and therapeutic potential" Clin Exp Dermatol 27: 571-577, 2002 and Jones, "Resiquimod 3M", *Curr Opin Investig Drugs* 4: 214-218, 2003. Human immunomodulators suitable for use as adjuvants in the invention can include cytokines, such as interleukins (e.g., IL-1, IL-2, IL-4, IL-5, IL-6, IL-7, IL-12, and the like), interferons (e.g., interferon-gamma), macrophage colony stimulating factor, and tumor necrosis factor.

Adjuvant Combinations: The adjuvents are used in come preferred embodiments as combinations. For example, adjuvant compositions can include: a saponin and an oil-in-water emulsion (WO99/11241); a saponin (e.g., QS21)+a non-toxic LPS derivative (e.g., 3 dMPL) (see WO94/00153); a saponin (e.g., QS21)+a non-toxic LPS derivative (e.g., 3 dMPL)+a cholesterol; a saponin (e.g., QS21)+3 dMPL+IL-12 (optionally+a sterol) (WO98/57659); combinations of 3 dMPL with, for example, QS21 and/or oil-in-water emulsions (See European patent applications 0835318, 0735898 and 0761231); SAF, containing 10% Squalane, 0.4% Tween 80, 5% pluronic-block polymer L121, and thr-MDP, either microfluidized into a submicron emulsion or vortexed to generate a larger particle size emulsion. Ribi adjuvant system (RAS), (Ribi Immunochem) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox); and one or more mineral salts (such as an aluminum salt)+a non-toxic derivative of LPS (such as 3 dPML).

Aluminum salts and MF59 are examples of adjuvants for use with injectable influenza vaccines. Bacterial toxins and bioadhesives are examples of adjuvants for use with mucosally-delivered vaccines, such as nasal vaccines. All adjuvants noted above and others as generally known in the art to one of ordinary skill can be formulated for intranasal administration using techniques well known in the art.

C. Formulations and Carriers

The composition of the invention can be formulated in pharmaceutical compositions. These compositions can comprise, in addition to one or more of the strains, a pharmaceutically acceptable excipient, carrier, buffer, stabilizer, or other materials well known to those skilled in the art. Such materials should typically be non-toxic and should not typically interfere with the efficacy of the active ingredient. The precise nature of the carrier or other material can depend on the route of administration, e.g., oral, intravenous, cutaneous or subcutaneous, nasal, intramuscular, or intraperitoneal routes.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil, or synthetic oil. Physiological saline solution, dextrose, or other saccharide solution or glycols such as ethylene glycol, propylene glycol, or polyethylene glycol can be included. The term "carrier" refers to a diluent, adjuvant, excipient, or vehicle with which the pharmaceutical composition (e.g., immunogenic or vaccine formulation) is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, ethanol and the like. Examples of suitable pharmaceutical carriers are described in "Remington's Pharmaceutical Sciences" by E. W. Martin. The formulation should be selected according to the mode of administration.

For intravenous, cutaneous, or subcutaneous injection, or injection at the site of affliction, the active ingredient will be in the form of a parenterally acceptable aqueous solution which is pyrogen-free and has suitable pH, isotonicity, and stability. Those of relevant skill in the art are well able to prepare suitable solutions using, for example, isotonic vehicles such as Sodium Chloride Injection, Ringer's Injection, or Lactated Ringer's Injection. Preservatives, stabilizers, buffers, antioxidants, and/or other additives can be included, as required.

Administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of disease being treated. Prescription of treatment, e.g., decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in the latest edition of Remington's Pharmaceutical Science, Mack Publishing Company, Easton, Pa. ("Remington's").

III. Methods of Making

A protocol to engineer AM/LAVIB/DelNS1 virus is provided. The protocol includes (a) generating influenza B virus with the coding region of the NS1 gene removed from its genome, by transfecting the eight plasmids, preferably pHW2000 plasmids, containing the genome of DelNS1 influenza B virus including a plasmid to express NS1 protein, into one or more vaccine producing cells with (b) rescuing LAVIB/DelNS1 virus and (c) passaging rescued virus into one or more vaccine producing cells at 33° C. and 37° C. respectively until viral titer is stabilized, for example, when the virus titer remains unchanged for three consecutive passages, to obtain AM/LAVIB/DelNS1 and (c) analyzing for the presence of desired mutations.

Whole sequence of growth-adapted DelNS1 influenza B virus was analyzed and compared to the sequence of parental strain, acquired mutations were identified. The coding region of the NS1 gene is removed from viral genome without affecting the expression of other essential genes for virus replication (illustrated in FIG. 1A). In a preferred embodiment, the virus in step b is cultured in a mixture of two or more cells, for example, 293T/MDCK cells. The disclosed methods for making LAIVB result in a deletion of the viral virulence element, the NS1 protein and an adaptive mutation which allows growth of the mutated strain in vaccine producing systems such as eggs and MDCK cells The preferred adaptive mutations are PA(T210C), NA T(1424C), NP(C182T) and M (A281G) mutations. The disclosed methods preferably include reverse genetics. Plasmids containing the deleted NS1 segment (DelNS1) and the other seven genome segments derived from an influenza B virus strain are transfected into 293T/MDCK cells mixture. Preferred virus strains include B/Yamagata and B/Victoria Rescued virus, passaged in MDCK cells until virus titer is stabilized, until high levels of viral titer are obtained and remain unchanged for at least three consecutive passages. The virus is sequenced to determine adaptive mutations.

The coding region of the NS1 gene can be removed using methods known in the art. Methods to introduce targeted mutations into a genome or, in the context of virology, into a virus are subsumed under the term reverse genetics (RG) and are disclosed for example, in Hoffmann et al., *Proc Natl Acad Sci USA*, 97(11):6108-13 Zheng et al., *J. Virol.* 89(20): 10273-85 and Dauber, et al., *J. Virol.*, 78(4):1865-1872 (2004), the materials and method of which are incorporated herein by reference. The method of generating influenza virus with the NS1 coding region deleted, as disclosed in Dauber et al. is generalized and summarized herein.

i. Generating Influenza B Virus with the Coding Region of the NS1 Gene Removed a. RT-PCR and Construction of Plasmids The RNeasy kit (Qiagen) can be used according to the manufacturer's protocol to extract viral RNA from a stock of influenza B virus. Eight reverse genetic plasmids pHW-PB2, pHW-PB1, pHW-PA, pHW-HA, pHW-NP, pHW-NA, pHW-M1, and pHW-NS1 (Table 1) are constructed by reverse transcriptase PCR (RT-PCR) amplification of single viral RNA segments and the resulting cDNAs cloned into the plasmid pHW2000. All eight plasmids can be used to generate the wild type influenza B virus. The primers used in the PCR amplification are listed in the following Table 2:

TABLE 2

| | |
|---|---|
| Flub-pb1-lic-S (SEQ ID NO: 9) | Ccgaagttgggggg AGCAGAAGCGGAGC |
| Flub-pb1-lic-as (SEQ ID NO 10) | GGCCGCCGGGTTATT AGTAGAAACACGAGC |
| Flub-pb2-lic-S (SEQ ID NO: 11) | Ccgaagttgggggg AGCAGAAGCGGAGC |
| Flub-pb2-lic-as (SEQ ID NO 12) | GGCCGCCGGGTTATT AGTAGAAACACGAGC |
| Flub-pa-lic-S (SEQ ID NO: 13) | Ccgaagttgggggg AGCAGAAGCGGTGC |
| Flub-pa-lic-as (SEQ ID NO 14) | GGCCGCCGGGTTATT AGTAGAAACACGTGC |
| Flub-ha-lic-S (SEQ ID NO 15) | Ccgaagttgggggg AGCAGAAGCAGAGC |
| Flub-ha-lic-as (SEQ ID NO: 16) | GGCCGCCGGGTTATT AGTAGTAACAAGAGC |
| Flub-na-lic-S (SEQ ID NO 17) | Ccgaagttgggggg AGCAGAAGCAGAGC |
| Flub-na-lic-as (SEQ ID NO: 18) | GGCCGCCGGGTTATT AGTAGTAACAAGAGC |
| Flub-np-lic-S (SEQ ID NO 19) | Ccgaagttgggggg AGCAGAAGCACAGC |

TABLE 2-continued

| | |
|---|---|
| Flub-np-lic-as (SEQ ID NO: 20) | GGCCGCCGGGTTATT AGTAGAAACAACAGC |
| Flub-m-lic-S (SEQ ID NO: 21) | Ccgaagttgggggg AGCAGAAGCACGCAC TT |
| Flub-m-lic-as (SEQ ID NO 22) | GGCCGCCGGGTTATT AGTAGAAACAACGCA CTT |
| Flub-ns-lic-S (SEQ ID NO: 23) | Ccgaagttgggggg AGCAGAAGCAGAGGA TT |
| Flub-ns-lic-as (SEQ ID NO 24) | GGCCGCCGGGTTATT AGTAGTAACAAGAGG ATT |
| Flub-delns1-F (SEQ ID NO: 25) | CTCAAT TT G TGTTGTGGTC ATG |
| Flub-delns1-R (SEQ ID NO: 26) | TGGAGGATGAAGAAG ATGGCCATCGGATCC TC |

The coding region of the influenza B virus NS1 protein overlaps in part with the reading frame for the NEP/NS2 protein that is expressed from a spliced transcript of the viral NS gene segment. For the generation of NS1-deficient influenza B virus, we prepared a derivative of the NS reverse genetic plasmid termed pHW-Lee-ΔNS1-B, in which the sequences specifying the NS1 protein were deleted, while all NEP/NS2 coding sequences and the terminal noncoding regions were maintained. For example, for generation of the pHW-DelNS1-B plasmid, polyadenylated RNA is extracted from influenza B virus-infected MDCK cells by using the Oligotex direct mRNA Midi/Maxi Kit (Qiagen) and NS segment-specific primers used for RT-PCR amplification. Amplified NEP/NS2 fragment is purified with the QiaEx II gel extraction kit (Qiagen), digested with BsmBI, and cloned into pHW2000.

These plasmids facilitate bidirectional transcription of negative-sense viral RNAs and positive-sense mRNAs since the cloned viral cDNAs are flanked upstream by a human RNA polymerase I promoter and downstream by an RNA polymerase II-specific promoter. In brief, the viral RNAs are first reverse transcribed with Moloney murine leukemia virus reverse transcriptase (Promega) by using a universal nine-nucleotide primer (UNI-9) that is complementary to the conserved 3' ends of all eight viral RNA segments. The RT reaction is performed for 60 min at 37° C., followed by 15 min at 70° C. Subsequently, single gene segments are amplified by PCR by using the Pfu Turbo Polymerase (Roche Diagnostics) and segment-specific primers carrying BsmBI (PB1, PB2, PA, NA, M, and NS), BspMI (NP), or AarI (HA) restriction site sequences at their 5' ends. pHW-NS-XhoI is a derivative of pHW-NS that is constructed with the QuikChange mutagenesis kit (Stratagene) by introducing a novel XhoI recognition site at nucleotides 262 to 267 of the viral NS segment. The NS segment of the transfectant virus is engineered to carry an engineered genetic tag site such that the corresponding cDNA is susceptible to cleavage by the restriction endonuclease XhoI, thereby verifying the recombinant nature of the isolate.

b. Transfection-Mediated Recovery of Recombinant Influenza B Virus.

To generate the recombinant influenza B wild-type virus the eight plasmids pHW-PB2, pHW-PB1, pHW-PA, pHW-HA, pHW-NP, pHW-NA, pHW-M, and pHW-NS-XhoI (0.5

µg each) are transfected into $10^6$ 293 T cells in suspension with the Lipofectamine 2000 reagent (Invitrogen). At 72 h after transfection, the supernatant of transfected cells is inoculated into the allantoic cavities of 11-day-old chicken eggs to grow stocks of recombinant virus. Supernatants of transfected cells harboring mutant plasmid can be passaged into 6-day-old chicken eggs. The recovery of recombinant influenza B viruses can be verified by gel electrophoretic analyses of RT-PCR products representing the viral NS segments.

The plasmids are preferably transfected into a mixture of cells, for example, 293T/MDCK cells to grow stocks of recombinant virus. FIG. 1A The DelNS1 virus can be rescued by essentially the same procedure, except that pHW-NS-XhoI is replaced by pHW-ΔNS1-B and 0.5 µg of an expression vector for NS1, for example, pcDNA-NS1 added to the transfection mix. To construct plasmid pcDNA-NS1-B, the NS1 cDNA can be PCR amplified with pHW-Lee-NS as a template and cloned between the HindIII/XhoI sites of pcDNA3

The influenza B virus completely lacking the NS1 ORF disclosed in Dauber, et al. *J. Virol.*, 78:1865-1872 (2004) does not replicate efficiently in Vero cells (titres of 1.7-2.5*$10^2$ FFU/ml using an moi of 0.1 and no detectable titres at moi of 0.001, respectively. An influenza B NS1 deletion mutant consisting of the amino-terminal 16 aa is also highly attenuated in replication with maximum titres of approx. $10^4$ FFU/ml. (Hai et. al; Journal of Virology; November 2008, p. 10580-90 ii. Culturing Rescued Virus to Obtain Influenza B Virus with Comparable Growth to Wild Type Rescued DelNS1 virus is cultured in a virus-producing cell until virus titer is stabilized, with evidence that virus titer remains unchanged for at least three consecutive passages in MDCK cells and eggs. Referring to FIG. 1A, supernatant from the transfected cells after 72 hours is collected and passaged in MDCK cells.

A preferred cell for passaging is MDCK (Madin-Darby canine kidney) cells. However, the cells used for the cultivation of viruses using a cultivation medium can be cells that can grow in vitro in synthetic media and can be used for the propagation of viruses. These can be for example BSC-1 cells, LLC-MK cells, CV-1 cells, CHO cells, COS cells, murine cells, human cells, HeLa cells, 293 cells, VERO cells, MDBK cells, MDOK cells, CRFK cells, RAF cells, TCMK cells, LLC-PK cells, PK15 cells, WI-38 cells, MRC-5 cells, T-FLY cells, BHK cells, SP2/0 cells, NS0, PerC6 (human retina cells), chicken embryo cells or derivatives, embryonated egg cells, embryonated chicken eggs or derivatives thereof.

The cultivation medium used for the production of viruses can be any medium known from prior art that is applicable for virus cultivation. Preferably the medium is a synthetic medium. This can be for example basal media as Modified Eagle's media MEM, minimum essential media MEM, Dulbecco's modified Eagle's media D-MEM, D-MEM-F12 media, William's E media, RPMI media and analogues and derivative thereof. These can also be specialty cell cultivation and virus growth media as VP-SFM, OptiPro™ SFM, AIM V® media, HyQ SFM4 MegaVir™, EX-CELL™ Vero SFM, EPISERF, ProVero, any 293 or CHO media and analogues and derivatives thereof. These media can be supplemented by any additive known from prior art that is applicable for cell and virus cultivation as for example animal sera and fractions or analogues thereof, amino acids, growth factors, hormones, buffers, trace elements, trypsin, sodium pyruvate, vitamins, L-glutamine and biological buffers. Preferable medium is OptiPRO™ SFM supplemented with L-glutamine and trypsin.

Thus, disclosed method includes culturing the virus in for an effective amount of time to obtain a stable viral titer. In preferred embodiment, the rescued virus is passaged in a virus-producing cell, for example, MDCK cells for a period of time until viral titre remains unchanged for 3 consecutive passaged. This culture period can range from 10-50 passages, preferably, for over 20 passages at 33° C. The time and conditions of culture result in adaptive mutations, which allows replication of the LAIVB in vaccine producing systems such as eggs or MDCK.

The examples demonstrate mutations in PA(T210C), NA(T1424C), NP (C182T) and M (A281G) which support DelNS1 flu B virus replication in chicken embryo eggs or the vaccine producing cell line, MDCK cells, for the viral strain tested (FIG. 1B). The DelNS1 flu B live attenuated virus with adaptive mutations is able to replicate to comparable level as wild type virus in vaccine producing systems, eggs or MDCK cells (FIG. 2B). The DelNS1 live attenuated is not able to replicate in interferon-competent cells, A549. This a safety property to prevent virus shedding in vaccinated humans (FIGS. 2C AND 2D). The DelNS1 flu B virus prefers to replicate at lower temperature, such as 33° C., which is mimics the upper respiratory tract, but replication is restricted at 37° C. (FIG. 2C), which the mimics the lower respiratory tract. This property in the DelNS1 flu B virus is an additional safety feature to be used as a vaccine in humans (FIG. 2C).

IV. Methods of Use

The disclosed AM/LAVIB/DelNS1 can be used to effectively increase viral titer or elicit an immune response in a subject in need thereof. In some aspects, subjects can include the elderly (e.g., >65 years old), young children (e.g., <5 years old). Methods for improving immune response in children using adjuvanted formulations are disclosed for example in U.S. Publication 2017/0202955.

The LAIVB can generally be administered directly to a mammal in need thereof to increase viral titer in the mammal and elicit an immune response. The Examples demonstrate that immunization of one lineage of flu B vaccine, Victoria lineage, is able to protect mice from lethal challenge of either Victoria or Yamagata lineage of mouse adapted flu B virus (FIGS. 3A and 3B).

Viruses are typically administered to a patient in need thereof in a pharmaceutical composition. Pharmaceutical compositions containing virus may be for systemic or local administration. Dosage forms for administration by parenteral (intramuscular (IM), intraperitoneal (IP), intravenous (IV) or subcutaneous injection (SC)), or transmucosal (nasal, vaginal, pulmonary, or rectal) routes of administration can be formulated. In the most preferred embodiments, the immunizing virus is delivered peripherally by intranasally or by intramuscular injection, and the therapeutic virus is delivered by local injection.

Direct delivery can be accomplished by parenteral injection (e.g., subcutaneously, intraperitoneally, intradermal, intravenously, intramuscularly, or to the interstitial space of a tissue), or mucosally, such as by rectal, oral (e.g., tablet, spray), vaginal, topical, transdermal (See e.g., WO99/27961) or transcutaneous (See e.g., WO02/074244 and WO02/064162), inhalation, intranasal (See e.g., WO03/028760), ocular, aural, pulmonary or other mucosal administration. Compositions can also be administered topically by direct transfer to the surface of the skin. Topical administration can be accomplished without utilizing any devices, or by contacting naked skin with the composition utilizing a bandage or a bandage-like device (see, e.g., U.S. Pat. No. 6,348,450). In some aspects, the mode of administration is parenteral, mucosal, or a combination of mucosal and parenteral immunizations. In other aspects, the mode of administration is parenteral, mucosal, or a combination of mucosal and parenteral immunizations in a total of 1-2 vaccinations 1-3 weeks apart. In related aspects, the route of administration includes but is not limited to intranasal delivery.

1. Effective Amounts

Typically the composition is administered in an effective amount to induce an immune response against a one or more antigens encoded by the virus. For example, an effective amount of virus generally results in production of antibody and/or activated T cells that kill or limit proliferation of or infection by the virus The composition can typically be used to elicit systemic and/or mucosal immunity, for example to elicit an enhanced systemic and/or mucosal immunity. For example, the immune response can be characterized by the induction of a serum IgG and/or intestinal IgA immune response. Typically, the level of protection against influenza infection can be more than 50%, e.g., 60%, 70%, 80%, 90%, 91%, 92%, 93%, 94%, 95%, 96%, 97%, 98%, 99%, or more. In one aspect, the level of protection can be 100%.

The immune response induced by the invention can be one or both of a TH1 immune response and a TH2 response. The immune response can be an improved or an enhanced or an altered immune response. The immune response can be one or both of a systemic and a mucosal immune response. For example, the immune response can be an enhanced systemic and/or mucosal response. An enhanced systemic and/or mucosal immunity is reflected in an enhanced TH1 and/or TH2 immune response. For example, the enhanced immune response can include an increase in the production of IgG1 and/or IgG2a and/or IgA. In another aspect the mucosal immune response can be a TH2 immune response. For example, the mucosal immune response can include an increase in the production of IgA.

Typically, activated TH2 cells enhance antibody production and are therefore of value in responding to extracellular infections. Activated TH2 cells can typically secrete one or more of IL-4, IL-5, IL-6, and IL-10. A TH2 immune response can also result in the production of IgG1, IgE, IgA, and/or memory B cells for future protection. In general, a TH2 immune response can include one or more of an increase in one or more of the cytokines associated with a TH2 immune response (such as IL-4, IL-5, IL-6 and IL-10), or an increase in the production of IgG1, IgE, IgA and memory B cells. For example, an enhanced TH2 immune response can include an increase in IgG1 production. A TH1 immune response can include one or more of an increase in CTLs, an increase in one or more of the cytokines associated with a TH1 immune response (such as IL-2, IFN-gamma, and TNF-alpha), an increase in activated macrophages, an increase in NK activity, or an increase in the production of IgG2a. For example, the enhanced TH1 immune response can include an increase in IgG2a production.

The LAIVB strains can be used either alone or in combination with other agents optionally with an immunoregulatory agent capable of eliciting a Th1 and/or Th2 response.

2. Dosages

The precise dosage will vary according to a variety of factors such as subject-dependent variables (e.g., age, immune system health, etc.), and age of the subject being treated. Appropriate dosages can be determined by a person skilled in the art, considering the therapeutic context, age, and general health of the recipient. The selected dosage depends upon the desired therapeutic effect, on the route of administration, and on the duration of the treatment desired. In determining the effective amount of the virus to be administered for the prophylaxis, the physician may evaluate circulating plasma levels of virus, and/or the production of existing antibodies against the antigen(s). Active virus can also be measured in terms of plaque-forming units (PFU). A plaque-forming unit can be defined as areas of cell lysis (CPE) in monolayer cell culture, under overlay conditions, initiated by infection with a single virus particle. Generally, dosage levels of virus between $10^2$ and $10^{12}$ pfu are administered to humans. In different embodiments, the dosage range is from $10^4$ to $10^{10}$ pfu, $10^5$ to $10^9$ pfu, $10^6$ to $10^8$ pfu, or any dose within these stated ranges. When more than one vaccine is to be administered (i.e., in combination vaccines), the amount of each vaccine agent can be within their described ranges.

Virus is typically administered in a liquid suspension, in a volume ranging between 10 µl and 100 µl depending on the route of administration. Vaccine volumes commonly practiced range from 0.1 mL to 0.5 mL. Generally, dosage and volume will be lower for local injection as compared to systemic administration or infusion.

The vaccine composition can be administered in a single dose or a multi-dose format. Vaccines can be prepared with adjuvant hours or days prior to administrations, subject to identification of stabilizing buffer(s) and suitable adjuvant composition. Typically, the dose will be 100 μl administered locally in multiple doses, while systemic or regional administration via subcutaneous, intramuscular, intra-organ, intravenous or intranasal administration can be from for example, 10 to 100 μl.

V. Kits

A kit including the disclosed LAIVB is also provided. The kit can include a separate container containing a suitable carrier, diluent or excipient, Additionally, the kit can include instructions for mixing or combining ingredients and/or administration. Compositions can be in liquid form or can be lyophilized. Suitable containers for the compositions include, for example, bottles, vials, syringes, and test tubes. Containers can be formed from a variety of materials, including glass or plastic. A container can have a sterile access port (for example, the container can be an intravenous solution bag or a vial having a stopper pierceable by a hypodermic injection needle).

The kit can further include a second container comprising a pharmaceutically-acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery device(s). The kit can further include a third component comprising an adjuvant.

The kit can also include a package insert containing written instructions for methods of inducing immunity, preventing infections, or for treating infections. The package insert can be an unapproved draft package insert or can be a package insert approved by the Food and Drug Administration (FDA) or other regulatory body. The invention also provides a delivery device pre-filled with the compositions of the invention.

The compositions are generally formulated as sterile, substantially isotonic and in full compliance with all Good Manufacturing Practice (GMP) regulations of the U.S. Food and Drug Administration.

EXAMPLES

Materials and Methods
Cells and Viruses

B/HK/8038/11 strain was obtained from Queen Mary Hospital and whole genome sequences of DelNS1 B/HK/8038/11 have been deposited in GenBank under accession no: MH636851-MH636858. All cell lines were obtained from ATCC. Human embryonic kidney cells (293T) and lung adenocarcinoma cells (A549) were maintained in Dulbecco's minimal essential medium (DMEM) supplemented with 10% fetal bovine serum, 100 units/ml penicillin, and 100 µg/ml streptomycin sulfate (Life Technologies). Canine MDCK cells were cultured in Eagle's minimal essential medium (MEM) supplemented with the same amount of serum and antibiotics. Influenza B virus B/HK/8038/11 was rescued by reverse genetics. B DelNS1(Flu B) LAIVs were constructed and rescued according to the protocols described here and in the previous report (Zheng, et al, *J. Virol.*, 89:10273-10285 (2015). Viral gene segments were amplified and cloned into pHW2000 plasmids, resulting in eight pHW2000 plasmids, which were transfected into 293T/MDCK cell mixtures. Rescued virus was amplified in MDCK cells or embryonated chicken eggs.

Construction of Plasmids

The NS1 deletion plasmid, pHW2000-DelNS1, was constructed as described before (Zheng, et al, *J. Virol.*, 89:10273-10285 (2015). Inverse PCR was performed to delete the NS1 gene using pHW2000-8038-NS (influenza B) plasmid as a template. The PCR product was then gel purified, phosphorylated and self-ligated using a standard protocol. Primers for influenza B DelNS1 424 inverse PCR were 5'-CTCAAT TT GTGTTGTGGTC ATG-3' (SEQ ID NO: 25) (Flub-DelNS1-F) and 5'-TGGAGGAT-GAAGAAGA TGGCCATCGG ATCCTC-3' (SEQ ID NO: 26) (Flub-DelNS1-R).

Example 1. Generation and Characterization of DelNS1 Influenza B Live Attenuated Virus Vaccine A clinical isolate, B/Hong Kong/8038/2011, which was confirmed to be the Victoria lineage by sequence analysis, was used in these experiments. Coding region of the NS1 gene was removed from viral genome without affecting the expression of other essential genes for virus replication (FIG. 1A).

Eight pHW2000 plasmids, containing the DelNS1 segment and the other 7 influenza virus segments, together with an NS1 expression plasmid, were transfected into a 293T/MDCK cell mixture and incubated overnight. The DNA mixture was removed and MEM supplemented with 1 µg/ml N-tosyl-L-phenylalanine chloromethyl ketone (TPCK)-treated trypsin (Sigma) added. Virus supernatant was collected 72 h later and designated passage 0 (P0) virus, and then subsequently passaged in MDCK cells or embryonated chicken eggs.

Initial rescued DelNS1-8308B influenza B virus, obtained from transfected 293T cells at 37° C. for 72 hours, only replicates poorly in MDCK cells or eggs. Rescued virus was passaged 10 times at 33° C. in MDCK cells. For all DelNS1 viruses, deletion of the NS1 gene was confirmed by RT-PCR and sequencing. Rescued virus (DelNS1-8308B influenza B virus) was in MDCK cells for more than 20 times at 33° C. and 30° C. respectively until virus titer was stabilized, measured as when the virus titer remains unchanged for three consecutive passages. This was followed by identification of adaptive mutations in growth adapted DelNS1-8308B influenza B virus. Four mutations in PA(T210C), NA T(1424C), NP(C182T) and M (A281G) were identified. The DelNS1-8308B influenza B virus, designated Influenza B virus DelNS1-B8038HK, has been deposited with the American Type Culture Collection, and has ATCC Deposit No. PTA-125209.

Example 2. Growth Properties of DelNS1 Flu B Virus in MDCK and A459 Cells

Growth kinetics of DelNS1 virus were estimated in MDCK and A549 cells at 37° C. and 33° C. degrees respectively. Confluent cells (A549 or MDCK) seeded in 24-well plates were infected with viruses at the indicated multiplicity of infection (MOI). After 1 h adsorption, viral supernatant was removed, the cells washed twice with phosphate-buffered saline (PBS), then overlaid with MEM containing 1 µg/ml TPCK trypsin and incubated at the indicated temperature. Supernatants were 447 collected at different time points and titered by plaque assay in MDCK cells.

Plaque assay: Viruses were 10-fold serially diluted and added to confluent MDCK cells in 6-well plates, then incubated at 37° C. for 1 h. Supernatant was removed and cells washed twice with PBS and then overlaid with 1% MEM agarose containing 1 µg/ml TPCK trypsin. Plates were incubated at 33° C. for 48 h and then fixed with 10% PBS buffered formaldehyde solution for at least 2 h. Plaques were visualized by staining with 1% crystal violet solution.

Figure 2B:
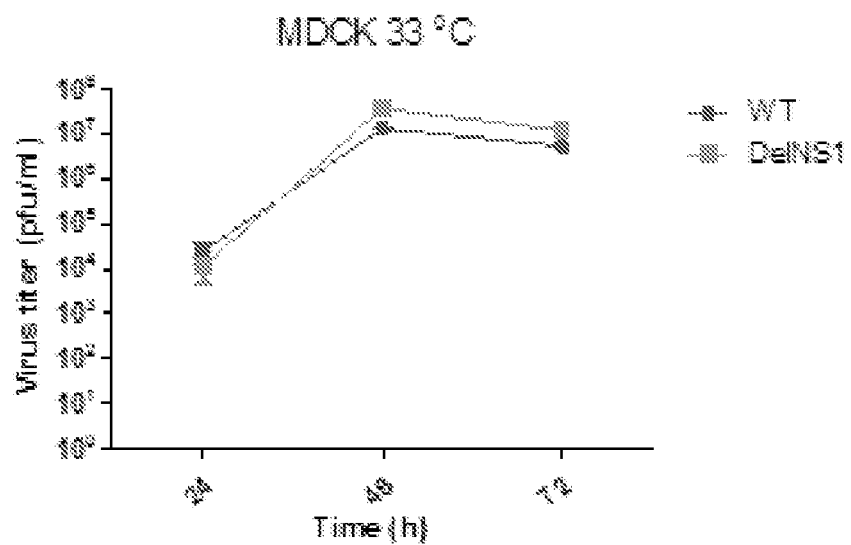
Figure 2C:
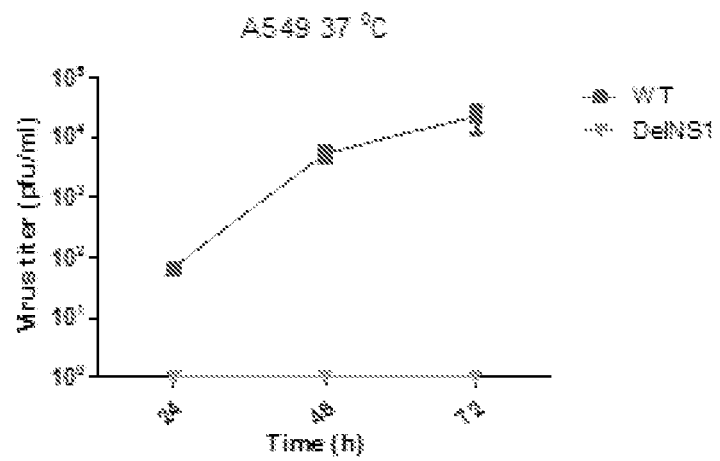
Figure 2D:
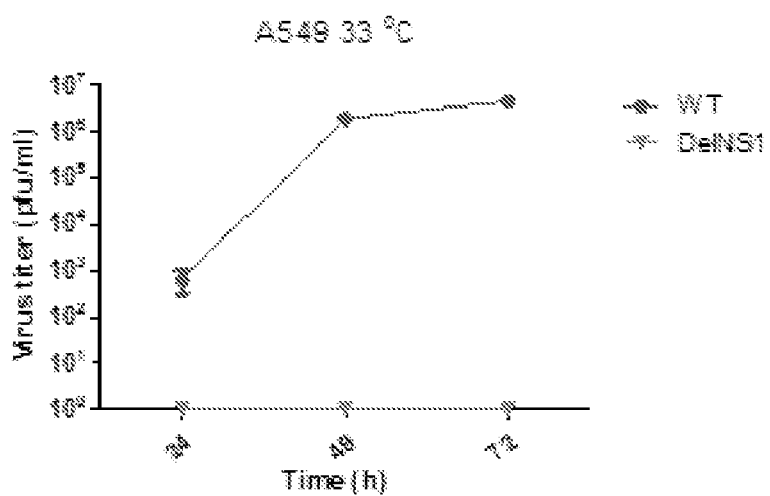

DelNS1 flu B live attenuated virus with adaptive mutations is able to replicate to comparable level as wild type virus in vaccine producing systems, eggs or MDCK cells (FIG. 2A). The DelNS1 live attenuated is not able to replicate in interferon-competent cells, A549. This a safety property to prevent virus shedding in vaccinated humans (FIG. 2B).

Growth kinetics of DelNS1-8308B influenza B virus carrying adaptive mutations was analyzed at 33° C. and 37° C. in MDCK cells. The DelNS1 flu B virus prefer to replicate at lower temperature, such as 33° C., which is mimics the upper respiratory tract, but replication is restricted at 37° C., which is the mimics the lower respiratory tract. This property in the DelNS1 flu B virus is an additional safety feature to be used as a vaccine in humans (FIG. 2B).

Example 3. Protection of Lethal Challenge by Mouse Adapted Flu B Viruses with DelNS1 Flu B Vaccine Mice were vaccinated with DelNS1 Flu B vaccine (Victoria lineage, $2 \times 10^6$ pfu) ONCE through nasal drop.

After three weeks, vaccinated mice were subsequently challenged with either one of mouse adapted flu B viruses, B/Florida/4/2006 (Yamagata lineage, $5 \times 10^5$ TCID$_{50}$)—and B/Brisbane/60/2008 (Victoria lineage, $5 \times 10^6$ TCID$_{50}$). Body weight and survival rate of the mice were recorded for 2 weeks. Mice with body weight loss greater than 25% were euthanized, in accordance with animal ethics guidelines. To evaluate viral replication in mouse lungs, lungs were collected at day 3 and homogenized in 1 ml PBS. Viral titers were determined by plaque assay in MDCK cells.

Figure 3C:
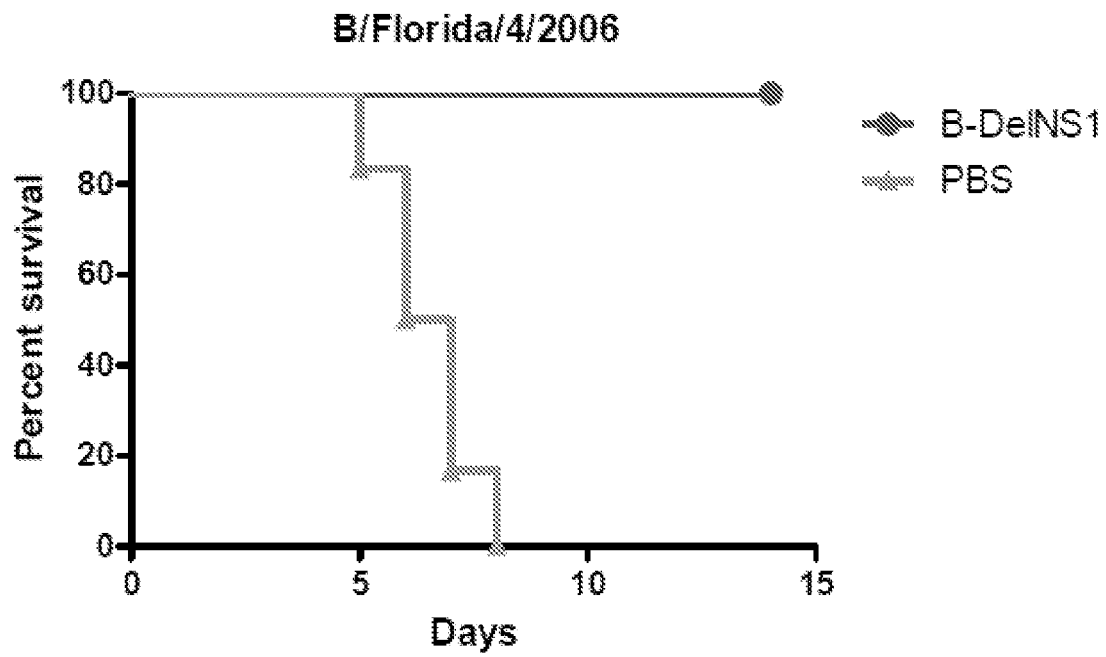
FIGS. 3C and 3D show percent survival of mice vaccinated with DelNS1 Flu B vaccine or PBS and challenged with B/Florida/4/2006 (FIG. 3C) or B/Brisbane/60/2008 (FIG. 3D).
Figure 3D:
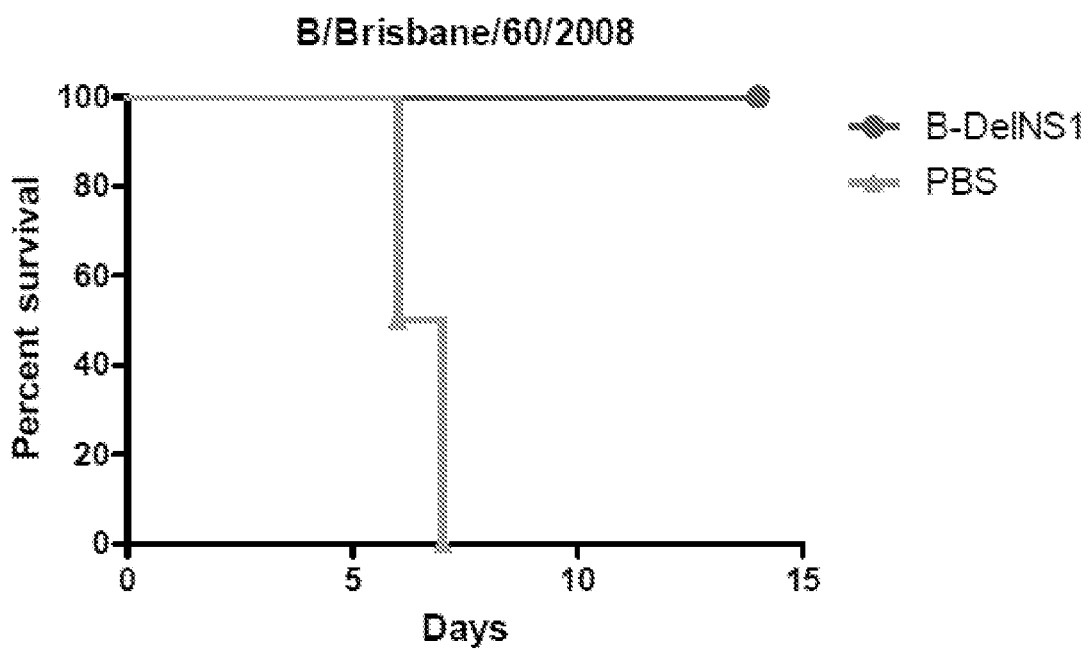
Figure 4A:
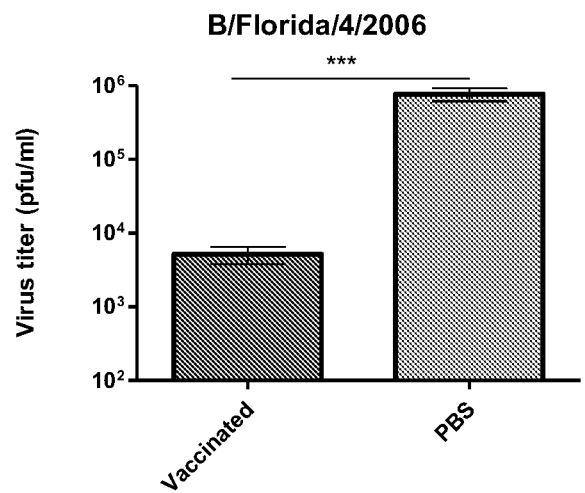
FIGS. 4A and 4B shows a comparison of viral titers in lungs of mice immunized with DelNS1 influenza B live attenuated virus vaccine and control (PBS mock vaccinated) on day 3 post infection of influenza B mouse adapted viruses, B/Florida/4/2006 (FIG. 4A) or B/Brisbane/60/2008 (FIG. 4B).
Figure 4B:
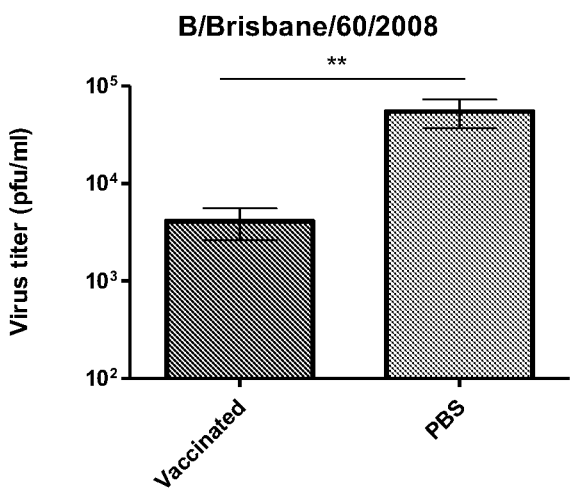

DelNS1 flu B virus is not virulent to mice, even when challenged with the highest dose of virus (FIGS. 3A and 3B). To assess if DelNS1-B8038, a Victoria lineage influenza B virus, protects from infection with both lineages of influenza B virus, mice were immunized once through the nasal route, then after three weeks challenged with mouse-adapted influenza B virus of either the Yamagata (B/Florida/4/2006) or Victoria (B/Brisbane/60/2008) lineage. Mice mock vaccinated with PBS died after 6-8 days, whereas all DelNS1-B8038 LAIV immunized mice survived (FIGS. 3C and 3D). Virus titers in lungs at day three post infection were significantly lower in DelNS1-B8038 LAIV vaccinated mice compared to the control group (FIGS. 4A and B). Immunization of one lineage of flu B live attenuated DelNS1 vaccine, DelNS1-B8038 of Victoria lineage, is able to protect mice from lethal challenge of either Victoria or Yamagata lineage of mouse adapted flu B virus (FIG. 3A-3D).

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "an aptamer" includes a plurality of such aptamers, reference to "the aptamer" is a reference to one or more aptamers and equivalents thereof known to those skilled in the art, and so forth.

Throughout the description and claims of this specification, the word "comprise" and variations of the word, such as "comprising" and "comprises," means "including but not limited to," and is not intended to exclude, for example, other additives, components, integers or steps.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. It should be understood that all of the individual values and sub-ranges of values contained within an explicitly disclosed range are also specifically contemplated and should be considered disclosed unless the context specifically indicates otherwise. Finally, it should be understood that all ranges refer both to the recited range as a range and as a collection of individual numbers from and including the first endpoint to and including the second endpoint. In the latter case, it should be understood that any of the individual numbers can be selected as one form of the quantity, value, or feature to which the range refers. In this way, a range describes a set of numbers or values from and including the first endpoint to and including the second endpoint from which a single member of the set (i.e. a single number) can be selected as the quantity, value, or feature to which the range refers. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Although the description of materials, compositions, components, steps, techniques, etc. may include numerous options and alternatives, this should not be construed as, and is not an admission that, such options and alternatives are equivalent to each other or, in particular, are obvious alternatives. Thus, for example, a list of different moieties does not indicate that the listed moieties are obvious one to the other, nor is it an admission of equivalence or obviousness.

We claim:

1. A composition comprising live attenuated influenza virus DeINS1-B8038HK.

2. The composition of claim 1, wherein the virus is not able to replicate in interferon-competent cells.

3. The composition of claim 2, wherein the interferon-competent cells are A549 cells.

4. The composition of claim 1, wherein the virus replicates poorly in MDCK cells at 37° C., when compared to its replication at 33° C. in the MDCK cells.

5. The composition of claim 1, wherein the virus is able to replicate at levels comparable to wild type influenza virus of the same strain, in a virus producing system, optionally, wherein between $10^7$ pfu/ml and $10^8$ pfu/ml of DeINS1-

B8038HK is recovered from the supernatant following passage in a virus producing system.

6. The composition of claim 5, wherein the virus producing system comprises MDCK cells culture.

7. The composition of claim 1, wherein administration of the virus to a subject in need thereof reduces viral titer of influenza B virus of a different strain in the subject infected with a different strain of influenza B virus.

8. A method for making the live attenuated influenza B virus (LAIVB) of claim 1, the method comprising: (a) generating influenza B virus B/Hong Kong/8038/2011, with deletion of the coding region of the NS1 coding region by transfecting cells with eight plasmids for genomic segments PA, PB1, PB2, NP, M, NS, HA and NA, wherein the plasmid coding for the NS genomic segment possesses a deletion of the NS1 gene (DelNS1) (b) rescuing virus from the transfected cells, which are LAIVB/DelNS1 and (c) passaging the rescued virus by culturing in one or more virus producing cells, to obtain AM/LAIVB/DelNS1;

wherein, the genomic segments of PA, NA, NP and M possess adaptive mutations (AM) T210C, T1424C, C182T and A281G, respectively.

9. The method of claim 8, wherein the genome of AM/LAIVB/DelNS1 is transfected into a 293T/MDCK cell mixture.

10. The method of claim 9, further comprising passaging rescued virus from the 293T/MDCK cell mixture in MDCK cells until virus titer is stabilized, wherein stabilized viral titer is measured as virus titer remaining unchanged for at least three consecutive passages in MDCK cells or embryonated chicken eggs.

11. A pharmaceutical composition comprising the composition of claim 1, in a pharmaceutically acceptable carrier, in an effective amount to induce an immune response to an antigen encoded by the virus's genome.

12. The pharmaceutical composition of claim 11, further comprising an adjuvant.

13. The pharmaceutical composition of claim 11, wherein the composition is suitable for nasal administration.

14. A method for increasing an immune response in a subject in need thereof, comprising administering the pharmaceutical composition of claim 11, to the subject.

\* \* \* \* \*